US012774489B2

United States Patent
(12) United States Patent
Manohar et al.

(10) Patent No.: US 12,774,489 B2
(45) Date of Patent: Oct. 27, 2026

(54) COMPOSITIONS AND METHODS FOR DETECTING SEVERE ACUTE RESPIRATORY SYNDROME CORONAVIRUS 2 (SARS-CoV-2) VARIANTS HAVING SPIKE PROTEIN MUTATIONS

(71) Applicant: Roche Molecular Systems, Inc., Pleasanton, CA (US)

(72) Inventors: Chitra Manohar, San Ramon, CA (US); Marcel R. Fontecha, San Ramon, CA (US); Christopher David Santini, Pleasant Hill, CA (US); Eugene Spier, Los Altos, CA (US); Jingtao Sun, San Ramon, CA (US); Michelle Elizabeth Yee, San Jose, CA (US); Kalyani Mangipudi, Pleasanton, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 844 days.

(21) Appl. No.: 17/692,955

(22) Filed: Mar. 11, 2022

(65) Prior Publication Data

US 2022/0290221 A1 Sep. 15, 2022

Related U.S. Application Data

(60) Provisional application No. 63/168,718, filed on Mar. 31, 2021, provisional application No. 63/161,398, filed on Mar. 15, 2021.

(51) Int. Cl.

*C12Q 1/6858* (2018.01)
*C12Q 1/6869* (2018.01)
*C12Q 1/6888* (2018.01)

(52) U.S. Cl.

CPC ......... *C12Q 1/6858* (2013.01); *C12Q 1/6869* (2013.01); *C12Q 1/6888* (2013.01)

(58) Field of Classification Search

CPC .. C12Q 1/6858; C12Q 1/6869; C12Q 1/6888; C12Q 1/6883; C12Q 1/701; C12Q 2600/156; C12Q 2600/16

See application file for complete search history.

(56) References Cited

U.S. PATENT DOCUMENTS 6,001,611 A * 12/1999 Will ........................ C07H 21/00 536/25.32
7,339,051 B2 3/2008 Crooke et al.

(Continued)

FOREIGN PATENT DOCUMENTS

CN 110982945 A 4/2020
CN 111254228 A 6/2020

(Continued)

OTHER PUBLICATIONS

Vanguilder, Twenty-Five Years of Quantitative PCR for Gene Expression Analysis, BioTechniques, May 2008, 44, 619-626 (Year: 2008).*

(Continued)

*Primary Examiner* — Robert T. Crow
*Assistant Examiner* — Allison E Schloop
(74) *Attorney, Agent, or Firm* — Daniel E. Agnew

(57) ABSTRACT

Methods for the rapid detection of the presence of variants of Severe Acute Respiratory Syndrome Coronavirus 2 (SARS-CoV-2) that contain mutations in the Spike (S) protein gene in a biological or non-biological sample are described. The methods can include performing an amplifying step, a hybridizing step, and a detecting step. Furthermore, primers and probes targeting SARS-CoV-2 variants containing S gene mutations and kits are provided that are (Continued)

designed for the detection of SARS-CoV-2 variants containing S gene mutations.

8 Claims, 4 Drawing Sheets

Specification includes a Sequence Listing.

(56) References Cited

U.S. PATENT DOCUMENTS

| | | | | |
|---|---|---|---|---|
| 7,736,850 | B2 | 6/2010 | Van Der Werf et al. | |
| 2015/0176060 | A1* | 6/2015 | Gupta | C12Q 1/6806 435/6.12 |
| 2015/0315636 | A1* | 11/2015 | Nadeau | C12Q 1/6858 435/6.11 |
| 2018/0291431 | A1* | 10/2018 | Paquette | C12Q 1/6895 |

FOREIGN PATENT DOCUMENTS

| | | | |
|---|---|---|---|
| CN | 111534643 | A | 8/2020 |
| CN | 111560478 | A | 8/2020 |
| CN | 112111597 | A | 12/2020 |
| CN | 113637798 | A | 11/2021 |
| JP | 2017518028 | A | 6/2017 |
| JP | 2018514202 | A | 6/2018 |
| RU | 2674338 | C1 | 12/2018 |
| WO | 2005092038 | A2 | 10/2005 |
| WO | 2014070946 | A1 | 5/2014 |
| WO | 2016172265 | A1 | 10/2016 |
| WO | 2021152181 | A1 | 8/2021 |
| WO | 2021188881 | A2 | 9/2021 |
| WO | 2021202158 | A1 | 10/2021 |
| WO | 2022020393 | A1 | 1/2022 |
| WO | 2022044011 | A1 | 3/2022 |

OTHER PUBLICATIONS

GenBank accession No. NC_045512.2 [online], GenBank, [Jul. 2020] [retrieved on Jul. 14, 2025]. Retrieved from: https://www.ncbi.nlm.nih.gov/nuccore/ NC_045512 (Year: 2020).*

BioSearch Technologies, Labeling oligonucleotides with internal BHQ dyes, [online], [2009] [retrieved on Jul. 14, 2025]. Retrieved from: https://web.archive.org/web/20161207193138/https://blog.biosearchtech.com/thebiosearchtechblog/bid/20308/labeling-oligos-with-internal-bhq-d (Year: 2009).*

You, Design of LNA probes that improve mismatch discrimination, Nucleic Acids Research, Apr. 2006, 34, 1-11 (Year: 2006).*

Nagy, Evaluation of TaqMan qPCR System Integrating Two Identically Labelled Hydrolysis Probes in Single Assay, Nature Scientific Reports, Jan. 2017, 7, 1-10 (Year: 2017).*

Lu, R. et al., "Genomic characterisation and epidemiology of 2019 novel coronavirus: implications for virus origins and receptor binding", the Lancet, Feb. 22, 2020, vol. 395, Issue 10224, pp. 565-574.

Wu, F. et al., "A new coronavirus associated with human respiratory disease in China", Nature, Mar. 12, 2020, vol. 579, pp. 265-269.

Corman, V.M. et al., "Detection of 2019 novel coronavirus (2019-nCOV) by real-time RT-PCR", Euro Surveill, Jan. 23, 2020, vol. 25(3), pp. 1-8.

Centers for Disease Control and Prevention (CDC), "2019-Novel Coronavirus (2019-nCOV) Real-time rRT-PCR Panel Primers and Probes" https://www.cdc.gov/coronavirus/2019-ncov/lab/rt-pcr-panel-primer-probes.html, effective Jan. 24, 2020.

"Investigation of novel SARS-COV-2 variant Variant of Concern 202012/01 Investigation of novel SARS-COV-2 variant", Dec. 21, 2020 (Dec. 21, 2020), pp. 1-11, XP055803098, Retrieved from the Internet <URL:https://assets.publishing.service.gov.uk/government/uploads/system/uploads/attachment_data/file/959438/Technical_Briefing_VOC_SH_NJL2_SH2.pdf>.

Tegally, H. et al., "Emergence and rapid spread of a new severe acute respiratory syndrome-related coronavirus 2 (SARS-CoV-2) lineage with multiple spike mutations in South Africa", MEDRXIV, Dec. 22, 2020 (Dec. 22, 2020), XP055803107, Retrieved from the Internet <URL:https://www.medrxiv.org/content/10.1101/2020.12.21.20248640v1.full.pdf>.

Anonymous, SNPsig® SARS-CoV-2 (201/501Y.V1) UK variant SNPsig® real-time PCR SARS-COV-2 mutation detection/ allelic discrimination kit, Feb. 1, 2021, pp. 1-10; https://www.genesig.com/assets/files/SNPsig_SARS_CoV_2_201_501YV1_HANDBOOK_1.pdf.

International Preliminary Report on Patentability, Sep. 28, 2023.

International Search Report (Partial) issued Jul. 18, 2022 in Application No. PCT/EP2022/056496, 18 pages.

International Search Report issued Nov. 7, 2022 in Application No. PCT/EP2022/056496, 29 pages.

Korukluoglu, G., et al., 40 minutes RT-qPCR Assay for Screening Spike N501Y and HV69-70del Mutations, bioRxiv, Jan. 26, 2021, pp. 1-17; www.biorxiv.org/content/10.1101/2021.01.26.428302v1.full.pdf, 428302v1.

Nie, H., et al., Ultrasensitive Quantification of Hepatitis B Virus A1762T/G1764A Mutant by a SimpleProbe PCR Using a Wild-Type-Selective PCR Blocker and a Primer-Blocker-Probe Partial-Overlap Approach, Journal of Clinical Microbiology, May 11, 2011, pp. 2440-2448, vol. 49, No. 7.

Schoenbrunner, N.J., et al., Covalent modification of primers improves PCR amplification specificity and yield, Biology Methods and Protocols, Jan. 1, 2017, pp. 1-10, vol. 2, No. 1.

Vogels, C.B.F., et al., PCR assay to enhance global surveillance for SARS-CoV-2 variants of concern, medRxiv, Mar. 12, 2021, pp. 1-14; www.medrxiv.org/content/10.1101/2021.01.28.21250486v2.full.pdf, 21250486v2.

Noerz et. al., Evaluation of a fully automated high-throughput SARS Cov-2 multiplex qPCR assay with build in screening fuctionality for DelHV69/70 and N501Y variants such as B.1.1.7, 2021, pp. 1-12.

* cited by examiner

COMPOSITIONS AND METHODS FOR DETECTING SEVERE ACUTE RESPIRATORY SYNDROME CORONAVIRUS 2 (SARS-CoV-2) VARIANTS HAVING SPIKE PROTEIN MUTATIONS

CROSS REFERENCE TO RELATED APPLICATIONS

This application claims the benefit of priority to U.S. Provisional Application No. 63/161,398, filed on Mar. 15, 2021, and U.S. Provisional Application No. 63/168,718, filed on Mar. 31, 2021, each of which is hereby incorporated in its entirety by reference.

REFERENCE TO SEQUENCE LISTING

This application contains a Sequence Listing submitted as an electronic text file named "36783_US2_ST25.txt", having a size in bytes of 16 kb, and created on Feb. 12, 2022.

FIELD OF THE INVENTION

The present disclosure relates to the field of viral diagnostics, and more particularly to the detection of variants of Severe Acute Respiratory Syndrome Coronavirus 2 (SARS-CoV-2) that contain mutations in the Spike (S) protein gene.

BACKGROUND OF THE INVENTION

Viruses of the family Coronaviridae possess a single stranded, positive-sense RNA genome ranging from 26 to 32 kilobases in length. Coronaviruses have been identified in several avian hosts, as well as in various mammals, including camels, bats, masked palm civets, mice, dogs, and cats. Novel mammalian coronaviruses are now regularly identified. For example, an HKU2-related coronavirus of bat origin was responsible for a fatal acute diarrhoea syndrome in pigs in 2018.

Among the several coronaviruses that are pathogenic to humans, most are associated with mild clinical symptoms, with two notable exceptions: severe acute respiratory syndrome (SARS) coronavirus (SARS-CoV), a novel betacoronavirus that emerged in Guangdong, southern China, in November, 2002, and resulted in more than 8000 human infections and 774 deaths in 37 countries during 2002-03; and Middle East respiratory syndrome (MERS) coronavirus (MERS-CoV), which was first detected in Saudi Arabia in 2012 and was responsible for 2494 laboratory-confirmed cases of infection and 858 fatalities since September, 2012, including 38 deaths following a single introduction into South Korea.

In late December, 2019, several patients with viral pneumonia were found to be epidemiologically associated with a market in Wuhan, in the Hubei province of China, where a number of non-aquatic animals such as birds and rabbits were also on sale before the outbreak. A novel, human-infecting coronavirus, initially named 2019 novel coronavirus (2019-nCoV), was identified with use of next-generation sequencing. This novel coronavirus is classified under the family Coronavirus, genus Betacoronavirus and subgenus Sarbecovirus and is described in "Genomic characterization and epidemiology of 2019 novel coronavirus: implications for virus origins and receptor binding" by Lu, R. et al., Lancet, 2020, Vol. 395, p. 565-574, hereby incorporated by reference in its entirety. As of Feb. 11, 2020, the World Health Organization (WHO) announced the formal name for the virus as Severe Acute Respiratory Syndrome Coronavirus 2 (SARS-CoV-2).

Several lines of research and product development strategies are being pursued in order to combat the spread of SARS-CoV-2 and to mitigate the morbidity and mortality associated with COVID-19. These include the development of mRNA, virus vector, and protein subunit vaccines, small molecule antivirals, immune modulators, and other non-pharmaceutical interventions. Vaccines that have been studied and developed to date are mostly focused on the viral envelope glycoprotein (Spike, S) and have been remarkably successful so far. In addition, monoclonal antibodies that target S have been developed as antivirals, and are effective treatments if administered soon after infection or symptom onset. Monoclonal antibodies can also be administered to uninfected individuals to prevent infection by SARS-CoV-2.

Like all RNA viruses, SARS-CoV-2 has a propensity to evolve in response to external selection pressures, due to an error-prone RNA-dependent RNA polymerase and large population sizes. While coronaviruses have a proof-reading function as part of the replicase complex, its high replication rate in each host and enormous population of infected people leads to the generation of a vast pool of viral variants from which more fit variants can emerge. Strong but incomplete inhibition of replication, which might occur in an infected person with partial immunity or treated with a single anti-S monoclonal antibody, is almost certain to result in the selection of SARS-CoV-2 variants with escape mutations in S that have higher replicative fitness than the wild-type virus in a population of susceptible hosts. Similarly, if a naturally occurring variant were to arise with increased ability to spread in an immunologically naïve population, it could out-compete the wild-type virus in a relatively short period of time.

A year plus into the pandemic from SARS-CoV-2, with uncontrolled global transmission and significant virus evolution, hundreds of variants have arisen. Some of these variants, deemed Variants of Concern (VOC) such as the United Kingdom (B.1.1.17), South African (B.1.351), Brazilian (P.1/B.1.1.248) and Variants of Interest (VOI) US [B.1.526 (NY) and B.1.427/B.1.429 (California, and Ohio)], may be more contagious and/or affect therapeutic or vaccine responses. Epidemiological and virological assessments have confirmed more transmissible VOC are now independently arising with first reports from the UK in December 2020, and quickly following this, reports out of South Africa showed a distinct lineage spreading rapidly, becoming the dominant lineage within weeks. Whilst the full significance of the mutations is yet to be determined, the genomic data, showing the rapid displacement of other lineages, suggest that this lineage may be associated with increased transmissibility. A variant from Brazil emerged in early December 2020, and by mid-January 2021, had already caused a massive resurgence in cases. The concerns with vaccines and related spike-mediated SARS-CoV-2 adaptation led to the need for epidemiologic and surveillance efforts for select VOC. Key mutations (del 69-70, N501Y, E484K) found in these emerging strains are being used to track the spread of these most concerning strains. Mutations in the SARS-CoV-2 Spike gene render the virus highly transmissible. Thus, there is a need in the art for a quick, reliable, specific, and sensitive method to detect the variants of SARS-CoV-2, particularly those that contain the 69-70 deletion (del 69-70) and mutations at N501Y and E484K in the Spike protein gene.

SUMMARY OF THE INVENTION

The present disclosure relates to methods for the rapid detection of the presence or absence of a SARS-CoV-2 variant having a Spike protein mutation in a biological or non-biological sample, for example, multiplex detection of the SARS-CoV-2 variant by qualitative or quantitative real-time reverse-transcription polymerase chain reaction (RT-PCR) in a single test tube. Embodiments include methods of detection of the SARS-CoV-2 variant that carry one or more of the mutations comprising of del 69-70, N501Y, and E484K, comprising performing a reverse transcription step and at least one cycling step, which may include an amplifying step and a hybridizing step. Furthermore, the present disclosure include primers, probes, and kits that are designed for the detection of the SARS-CoV-2 variant in a single tube.

In one aspect, a method for detecting a SARS-CoV-2 variant having a Spike protein mutation in a sample is provided, comprising performing an amplifying step including contacting the sample with a set of primers to produce an amplification product if SARS-CoV-2 nucleic acid is present in the sample; performing a hybridizing step including contacting the amplification product with one or more detectable probes; and detecting the presence of the amplification product, wherein detection of the amplification product is indicative of the presence of the SARS-CoV-2 variant in the sample; wherein the set of primer comprises a first primer comprising or consisting of a first oligonucleotide sequence selected from the group consisting of SEQ ID NOs: 1-5 or a complement thereof; and a second primer comprising or consisting of a second oligonucleotide sequence selected from the group consisting of SEQ ID NOs: 7-14, or a complement thereof; wherein the one or more detectable probes comprises or consists of a third oligonucleotide sequence selected from the group consisting of SEQ ID NOs: 16-25, or a complement thereof; and wherein the Spike protein mutation is selected from a 69-70 deletion (del 69-70), a N501Y mutation, or a E484K mutation, or combinations thereof. In one embodiment, the steps are performed in the presence of one or more blocking oligonucleotide probes. In a further embodiment, the one or more blocking oligonucleotide probes comprise or consist of the oligonucleotide sequence of SEQ ID NOs: 37, 38 or 39, or any combinations thereof.

In another aspect, a multiplex method for detecting a SARS-CoV-2 variant having a Spike protein mutation in a sample is provided, comprising performing an amplifying step comprising contacting the sample with at least two sets of primers to produce first and second amplification products if the SARS-CoV-2 nucleic acid is present in the sample; performing a hybridizing step comprising contacting the amplification products with at least two detectable probes hybridizing to the first and second amplification products produced by the at least two sets of primers; and detecting the presence of at least one amplification product, wherein the presence of the at least one amplification product is indicative of the presence of the SARS-CoV-2 variant in the sample; and wherein a first set of primers comprises a forward primer comprising or consisting of an oligonucleotide sequence of SEQ ID NO: 1, and a reverse primer comprising or consisting of an oligonucleotide of SEQ ID NOs: 7 or 8; and a second set of primers comprises a forward primer comprising or consisting of an oligonucleotide sequence of SEQ ID NO: 2, and a reverse primer comprising or consisting of an oligonucleotide sequence of SEQ ID NOs: 9, 10 or 11; and wherein a first detectable probe hybridizing to the first amplification product produced by the first set of primers comprises or consists of an oligonucleotide sequence selected from the group consisting of SEQ ID NOs: 16-17, or a complement thereof; and wherein a second detectable probe hybridizing to the second amplification product produced by the second set of primers comprises or consists of an oligonucleotide sequence selected from the group consisting of SEQ ID NOs: 18-20, or a complement thereof; and wherein the Spike protein mutation is selected from a 69-70 deletion (del 69-70), a N501Y mutation, or a E484K mutation, or combinations thereof. In one embodiment, the steps are performed in the presence of one or more blocking oligonucleotide probes comprising or consisting of the oligonucleotide sequence of SEQ ID NOs: 37, 38 or 39, or any combinations thereof.

Herein, the SARS CoV-2 variant is selected from a 69-70 deletion (del 69-70), a N501Y mutation, or a E484K mutation, or a combinations thereof in the Spike protein as a result of the respective mutations and deletion in the S gene. In some embodiments, the first or second detectable probe specifically hybridizes to the S gene sequence that causes the 69-70 deletion of SARS-CoV-2. In some embodiments, the first or second detectable probe specifically hybridizes to the S gene sequence that causes the N501Y mutation of SARS-CoV-2. In some embodiments, the first or second detectable probe specifically hybridizes to the S gene sequence that causes the E484K mutation of SARS-CoV-2. In one embodiment, the one or more blocking probes comprises or consist of oligonucleotide sequences that are perfectly matched with the S gene sequence that is wild type at amino acid position 69-70, or at amino acid position 484 or at amino acid position 501 of the Spike protein. In some embodiment, the one or more blocking probes comprise or consist of the oligonucleotide sequence of SEQ ID NOs: 37, 38 or 39, and combinations thereof. In a further embodiment, a set of primers that amplifies specific nucleic acid sequences from the non-structural Open Reading Frame (ORF1a/b) of SARS-CoV-2 and a detectable probe that hybridizes to and detects an ORF1a/b amplification product generated by the set of primers are provided. In one embodiment, the set of primers comprises a forward primer comprising or consisting of an oligonucleotide sequence of SEQ ID NO: 6 and a reverse primer comprising or consisting of an oligonucleotide sequence of SEQ ID NO: 15; and the detectable probe comprises or consists of an oligonucleotide sequence of SEQ ID NO: 36, or a complement thereof.

In one embodiment, the set of primers for amplification of the SARS-CoV-2 variant includes a first primer comprising or consisting of an oligonucleotide sequence of SEQ ID NO: 1, and a second primer comprising or consisting of an oligonucleotide sequence of SEQ ID NO: 7 or 8, and a detectable probe that comprises or consists of an oligonucleotide sequence of SEQ ID NO: 16 or 17, or a complement thereof. In another embodiment, the first primer comprises or consists of an oligonucleotide sequence selected from the group consisting of SEQ ID NO: 2, the second primer comprises or consists of an oligonucleotide sequence of SEQ ID NOs: 9-11, and a detectable probe that comprises or consists of an oligonucleotide sequence of SEQ ID NO: 18-20, or a complement thereof. In one embodiment, the first primer comprises or consists of an oligonucleotide sequence of SEQ ID NO: 1, the second primer comprises or consists of an oligonucleotide sequence of SEQ ID NO: 8, and the detectable probe comprises or consists of an oligonucleotide sequence of SEQ ID NO: 17, or a complement thereof. In another embodiment, the first primer comprises or consists of an oligonucleotide sequence of SEQ ID NO: 2, the second primer comprises or consists of an oligonucleotide sequence of SEQ ID NO: 10, and the detectable probe comprises or consists of an oligonucleotide sequence of SEQ ID NO: 19, or a complement thereof. In yet another embodiment, the first primer comprises or consists of an oligonucleotide sequence of SEQ ID NO: 2, the second primer comprises or consists of an oligonucleotide sequence of SEQ ID NO: 10, and the detectable probe comprises or consists of an oligonucleotide sequence of SEQ ID NO: 20, or a complement thereof.

Other aspects of the disclosure provide an oligonucleotide comprising or consisting of a sequence of nucleotides selected from SEQ ID NOs: 1-39, or a complement thereof, which oligonucleotide has 100 or fewer nucleotides. In another aspect, the present disclosure provides an oligonucleotide that includes a nucleic acid having at least 70% sequence identity (e.g., at least 75%, 80%, 85%, 90% or 95%, etc.) to one of SEQ ID NOs: 1-39, or a complement thereof, which oligonucleotide has 100 or fewer nucleotides. Generally, these oligonucleotides may be primer nucleic acids, probe nucleic acids, or the like in these embodiments. In certain aspects, the oligonucleotides have 40 or fewer nucleotides (e.g., 35 or fewer nucleotides, 30 or fewer nucleotides, 25 or fewer nucleotides, 20 or fewer nucleotides, 15 or fewer nucleotides, etc.) In some aspects, the oligonucleotides comprise at least one modified nucleotide, e.g., to alter nucleic acid hybridization stability relative to unmodified nucleotides. Optionally, the oligonucleotides comprise at least one label and optionally at least one quencher moiety.

In one aspect, amplification can employ a polymerase enzyme having 5' to 3' nuclease activity. Thus, the donor fluorescent moiety and the acceptor moiety, e.g., a quencher, may be within no more than 5 to 20 nucleotides (e.g., within 8 or 10 nucleotides) of each other along the length of the probe. In another aspect, the probe includes a nucleic acid sequence that permits secondary structure formation. Such secondary structure formation may result in spatial proximity between the first and second fluorescent moiety. According to this method, the second fluorescent moiety on the probe can be a quencher.

In one aspect, the detectable probes for detecting a SARS CoV-2 variant may be labeled with a fluorescent dye which acts as a reporter. The probe may also have a second dye which acts as a quencher. The reporter dye is measured at a defined wavelength, thus permitting detection and discrimination of the amplified SARS-CoV-2 target. The fluorescent signal of the intact probes is suppressed by the quencher dye. During the PCR amplification step, hybridization of the probes to the specific single-stranded DNA template results in cleavage by the 5' to 3' nuclease activity of the DNA polymerase resulting in separation of the reporter and quencher dyes and the generation of a fluorescent signal. With each PCR cycle, increasing amounts of cleaved probes are generated and the cumulative signal of the reporter dye is concomitantly increased. Optionally, one or more additional probes (e.g., such as an internal reference control or other targeted probe (e.g., other viral nucleic acids) may also be labeled with a reporter fluorescent dye, unique and distinct from the fluorescent dye label associated with the SARS-CoV-2 probe. In such case, because the specific reporter dyes are measured at defined wavelengths, simultaneous detection and discrimination of the amplified SARS-CoV-2 target and the one or more additional probes is possible.

The present disclosure also provides for methods of detecting the presence or absence of a SARS-CoV-2 variant, or a SARS-CoV-2 nucleic acid containing a mutation or deletion in the Spike protein gene, in a biological sample from an individual. These methods can be employed to detect the presence or absence of SARS-CoV-2 variant or SARS-CoV-2 having a Spike gene mutation or deletion in nasopharyngeal (NSP) and oropharyngeal swab samples, for use in diagnostic testing. Additionally, the same test may be used by someone experienced in the art to assess other sample types to detect SARS-CoV-2 variants or SARS-CoV-2 Spike gene mutations and deletions. Such methods generally include performing a reverse transcription step and at least one cycling step, which includes an amplifying step and a dye-binding step. Typically, the amplifying step includes contacting the sample with a plurality of pairs of oligonucleotide primers to produce one or more amplification products if a nucleic acid molecule is present in the sample, and the dye-binding step includes contacting the amplification product with a double-stranded DNA binding dye. Such methods also include detecting the presence or absence of binding of the double-stranded DNA binding dye into the amplification product, wherein the presence of binding is indicative of the presence of SARS-CoV-2 variants or SARS-CoV-2 Spike gene mutations and deletions in the sample, and wherein the absence of binding is indicative of the absence of SARS-CoV-2 variants or SARS-CoV-2 Spike gene mutations and deletions in the sample. A representative double-stranded DNA binding dye is ethidium bromide. Other nucleic acid-binding dyes include DAPI, Hoechst dyes, PicoGreen®, RiboGreen®, OliGreen®, and cyanine dyes such as YO-YO® and SYBR® Green. In addition, such methods also can include determining the melting temperature between the amplification product and the double-stranded DNA binding dye, wherein the melting temperature confirms the presence or absence of SARS-CoV-2 variants or SARS-CoV-2 nucleic acid mutations and deletions.

In a further aspect, a kit for detecting one or more Spike gene mutations from SARS-CoV-2 variants is provided. The kit can include one or more sets of primers specific for amplification of the gene target; and one or more detectable oligonucleotide probes specific for detection of the amplification products.

In one aspect, the kit can include probes already labeled with donor and corresponding acceptor moieties, e.g., another fluorescent moiety or a dark quencher, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of SARS-CoV-2 Spike gene mutations and deletions in a sample.

In one aspect, a method is provided for allele-specific amplification of a target sequence, which exists in the form of several variant sequences in a sample, including providing a blocking oligonucleotide comprising a 5' terminus, a 3' terminus, and at least one nucleotide that is a locked nucleic acid (LNA), the blocking oligonucleotide being perfectly complementary to a wild type (WT) sequence when hybridized forming a first complex having a first melting temperature (Tm), the blocking oligonucleotide being partially non-complementary, at one or more nucleotides, to a target mutant (MT) sequence when hybridized forming a second complex having a second melting temperature (Tm), wherein the first Tm is higher than the second Tm, the blocking oligonucleotide being blocked at the 3 terminus prohibiting extension; and performing an amplifying step at a temperature higher than the second Tm but lower than the first Tm, the amplifying step comprising contacting the sample with a set of primers to produce an amplification product if the WT sequence and/or the target MT sequence is present in the sample, wherein the blocking oligonucleotide becomes unhybridized from the target MT sequence during the amplification step but remains hybridized with the WT sequence inhibiting amplification of the WT sequence.

In another aspect, a kit is provided for allele-specific amplification of a target sequence, which exists in the form of several variant sequences, including a set of primers; and a blocking oligonucleotide comprising a 5' terminus, a 3' terminus, and at least one nucleotide that is a locked nucleic acid (LNA), the blocking oligonucleotide being perfectly complementary to a wild type (WT) sequence when hybridized forming a first complex having a first melting temperature (Tm), the blocking oligonucleotide being partially non-complementary, at one or more nucleotides, to a target mutant (MT) sequence when hybridized forming a second complex having a second melting temperature (Tm), wherein the first Tm is higher than the second Tm.

In another aspect, an oligonucleotide is provided for performing an allele-specific amplification of a target sequence, which exists in the form of several variant sequences, including a sequence a 5' terminus and a 3' terminus being blocked at the 3' terminus prohibiting extension, the sequence being perfectly complementary to a wild type (WT) sequence when hybridized forming a first complex having a first melting temperature (Tm), and being partially non-complementary, at one or more nucleotides, to a target mutant (MT) sequence when hybridized forming a second complex having a second melting temperature (Tm), wherein the first Tm is higher than the second Tm; and at least one nucleotide that is a locked nucleic acid (LNA).

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

DETAILED DESCRIPTION OF THE INVENTION

Figure 1:
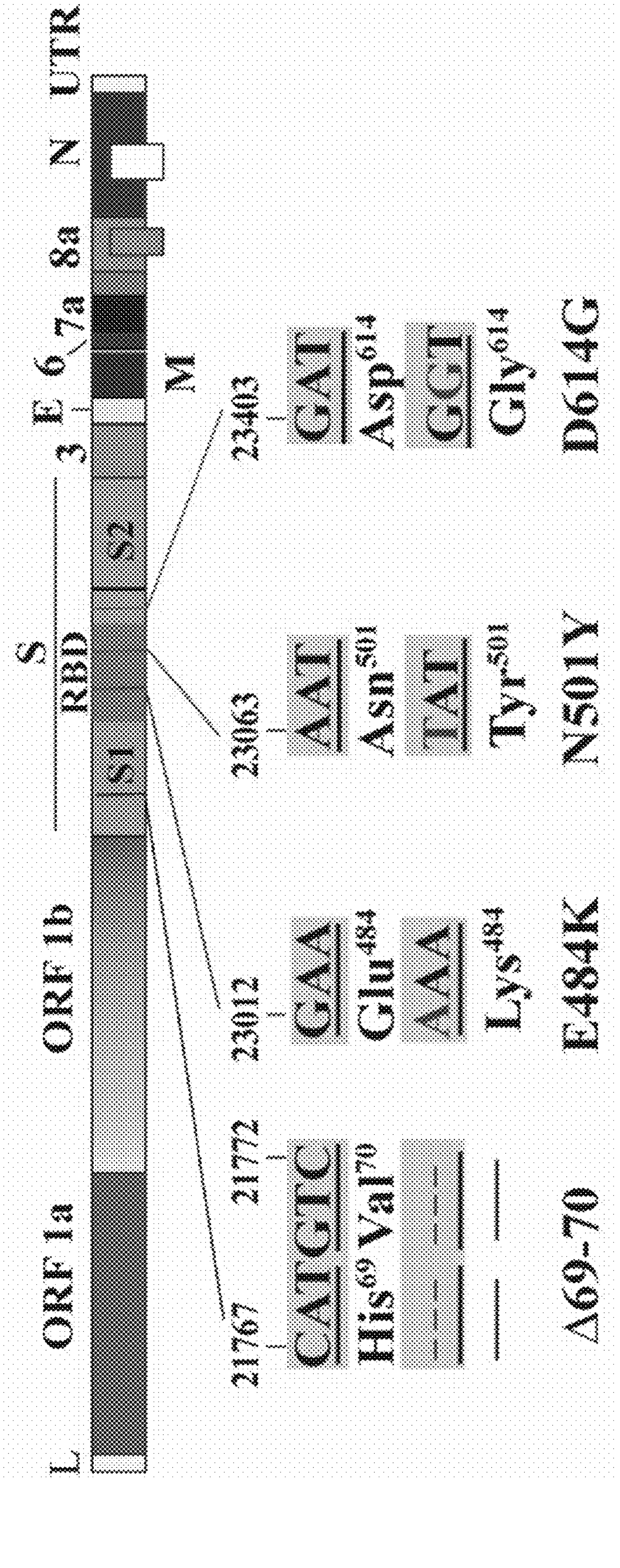
FIG. 1 shows the deletion and mutations of the Spike protein gene of the present disclosure and their locations within the SARS-CoV-2 genome. ORF, open reading frame; S, spike protein; RBD, receptor-binding domain.

Diagnosis of SARS-CoV-2 infection, both wild-type and variants, by nucleic acid amplification provides a method for rapidly, accurately, reliably, specifically, and sensitively detecting the viral infection. A real-time reverse-transcriptase PCR assay for detecting SARS-CoV-2 variants having a Spike protein gene mutation in a non-biological or biological sample is described herein. Primers and probes for detecting SARS-CoV-2 variants are provided, as are articles of manufacture or kits containing such primers and probes. The increased specificity and sensitivity of real-time PCR for detection of SARS-CoV-2 variants compared to other methods, as well as the improved features of real-time PCR including sample containment and real-time detection of the amplified product, make feasible the implementation of this technology not only for routine diagnosis of SARS-CoV-2 infections but also infections from SARS-CoV-2 variants in the clinical laboratory. Additionally, this technology may be employed for in vitro diagnostics as well as for prognosis. This SARS-CoV-2 variant detection assay may also be multiplexed with other assays for the detection of other nucleic acids, e.g., influenza virus, SARS-CoV, MERS-CoV, in parallel.

The SARS-CoV-2 genome is a positive sense single-stranded RNA molecule 29,903 bases in length (as shown in GenBank Accession No. NC_045512) with the order of genes (5' to 3') as follows: replicase ORF1ab (21,291 bases with 16 predicted non-structural proteins that are essential for viral replication and viral assembly), spike (S gene, 3,822 bases coding for spike protein responsible for binding to cell receptor), ORF3ab (828 bases in length), envelope (E gene, 228 bases coding for envelope protein), membrane (M gene, 669 bases coding for membrane protein), nucleocapsid (N gene, 1260 bases coding for nucleocapsid protein that forms complexes with the genomic RNA). In addition, there is 265 bases of non-coding region at the 5' terminal end and 229 bases of non-coding region at the 3' terminal end.

The S gene encodes the Spike protein, also referred to as the S protein or the Surface glycoprotein, which is transmembrane glycosylated protein, is composed of 1273 amino acid that assembles as a homotrimer and forms the spikes that protrude from the SARS-CoV-2 virus envelope. The Spike protein mediates viral entry into host cells by first binding to a host receptor through the receptor-binding domain (RBD) in the S1 subunit and then fusing the viral and host membranes through the S2 subunit. Similar to SARS-CoV, SARS-CoV-2 recognizes angiotensin-converting enzyme 2 (ACE2) as its host receptor binding to viral S protein. The RBD of the Spike protein in SARS-CoV-2 has been characterized as an approximately 200 amino acid region at residues 331 to 524 (or residues 333 to 527 in other reports).

Recent findings have reported the emergence of S gene variants that exhibit greater infectivity, high viral loads, potentially increased case fatality rates coupled with the decreased neutralization by antibodies generated by vaccines using the wildtype S target. These variants of concern (VOC) are UK B1.1.7 (69-70del, N501Y among others), the South African B.1.351 (K417N, E484K and N501Y) and the Brazilian B.1.1.28 (E484K, N501Y) and P1. These variants were detected by sequencing samples following PCR based detection. The locations of the 69-70 del, N501Y and E484K mutations as well as the commonly observed D614G mutation are shown in FIG. 1

The present disclosure includes oligonucleotide primers and fluorescent labeled hydrolysis probes that hybridize to the Spike protein gene of the SARS-CoV-2 genome in order to specifically identify SARS-CoV-2 variants using, e.g., TaqMan® amplification and detection technology. The oligonucleotides specifically hybridize to the S gene. The present disclosure also oligonucleotide primers and hydrolysis probers that hybridize to other regions in the SARS-CoV-2 genome (e.g. the ORF1ab gene) since having oligonucleotides that hybridize to multiple locations in the genome is advantageous for improved sensitivity compared to targeting only a single gene locus.

The disclosed methods may include performing a reverse transcription step and at least one cycling step that includes amplifying one or more portions of the nucleic acid molecule gene target from a sample using one or more pairs of primers. "SARS-CoV-2 primer(s)" as used herein refer to oligonucleotide primers that specifically anneal to nucleic acid sequences found in the SARS-CoV-2 genome, and initiate DNA synthesis therefrom under appropriate conditions producing the respective amplification products. Examples of nucleic acid sequences found in the SARS-CoV-2 genome, include nucleic acids within the ORF1ab gene, the S gene, the ORF3ab gene, the E gene, the M gene and the N gene and other predicted ORF regions. Each of the discussed SARS-CoV-2 primers anneals to a target region such that at least a portion of each amplification product contains nucleic acid sequence corresponding to the target. The one or more amplification products are produced provided that one or more nucleic acid is present in the sample, thus the presence of the one or more amplification products is indicative of the presence of SARS-CoV-2 in the sample. The amplification product should contain the nucleic acid sequences that are complementary to one or more detectable probes for SARS-CoV-2. "SARS-CoV-2 probe(s)" as used herein refer to oligonucleotide probes that specifically anneal to nucleic acid sequences found in the SARS-CoV-2 genome. Each cycling step includes an amplification step, a hybridization step, and a detection step, in which the sample is contacted with the one or more detectable SARS-CoV-2 probes for detection of the presence or absence of SARS-CoV-2 in the sample.

As used herein, the term "amplifying" refers to the process of synthesizing nucleic acid molecules that are complementary to one or both strands of a template nucleic acid molecule (e.g., nucleic acid molecules from the SARS-CoV-2 genome). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'—OH group where further "nucleotides" may be attached by a template-dependent DNA polymerase establishing 3' to 5' phosphodiester linkage whereby deoxynucleoside triphosphates are used and whereby pyrophosphate is released.

The term "hybridizing" refers to the annealing of one or more probes to an amplification product. "Hybridization conditions" typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished, if necessary.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a t-butyl benzyl, a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl ribo-U, 2'-0-methyl ribo-C, an N4-ethyl-dC, an N6-methyl-dA, and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. Nucleoside modifications may also include moieties that increase the stringency of hybridization or increase the melting temperature of the oligonucleotide probe. For example, a nucleotide molecule may be modified with an extra bridge connecting the 2' and 4' carbons resulting in "locked nucleic acid (LNA)" nucleotide that is resistant to cleavage by a nuclease (as described in Imanishi et al., U.S. Pat. No. 6,268,490 and in Wengel et al., U.S. Pat. No. 6,794,499, both of which are incorporated herein by reference in their entireties). To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference. Other modified nucleotide substitutions may alter the stability of the oligonucleotide, or provide other desirable features.

Detection of SARS-CoV-2

The present disclosure provides methods to detect SARS-CoV-2 variant having a Spike protein mutation by amplifying, for example, a portion of the SARS-CoV-2 S gene nucleic acid sequence. Nucleic acid sequences of the SARS-CoV-2 genome are available (e.g., GenBank Accession No. NC_045512, where the S gene is located at nucleotide positions 21563 to 25384). Specifically, primers and probes to amplify and detect SARS-CoV-2 S gene mutation and deletion target sequences are provided by the embodiments in the present disclosure.

For detection of SARS-CoV-2 VOCs, primers that amplify the S gene and probes that specifically detect mutations and deletions in the S gene are provided. SARS-CoV-2 nucleic acids other than those exemplified herein can also be used to detect SARS-CoV-2 variants in a sample. For example, functional variants can be evaluated for specificity and/or sensitivity by those of skill in the art using routine methods. Representative functional variants can include, e.g., one or more deletions, insertions, and/or substitutions in the SARS-CoV-2 nucleic acids disclosed herein.

More specifically, embodiments of the oligonucleotides each include a nucleic acid with a sequence selected from SEQ ID NOs: 1-5, 7-14, and 16-25, or a complement of SEQ ID NOs: 1-5, 7-14, and 16-25. In some embodiments, oligonucleotide probes that block the detection of wild-type (e.g. wild-type residues 69-70, E484, N501) selected from SEQ ID NOs: 37-39 are provided.

TABLE 1

SARS-CoV-2 Forward Primers
Forward Primers

| Oligo Name | SEQ ID NO: | Sequence | Modifications |
|---|---|---|---|
| D69-70_21690_F | 1 | TCAGATCCTCAGTTTTACATTCAACTCJ | J = t-butylbenzyl dA |
| E484K_23004F | 2 | GCCGGTAGCACACCTTGTAJ | J = t-butylbenzyl dA |
| Y144_F | 3 | GAAGACCCAGTCCCTACTTATTGTTAJ | J = t-butylbenzyl dA |
| K417_N439_L452_F1 | 4 | TGAAGTCAGACAAATCGCTCCJ | J = t-butylbenzyl dA |
| K417_N439_L452_F2 | 5 | ACAAATCGCTCCAGGGCAJ | J = t-butylbenzyl dA |
| NCOV-1-FN1.A | 6 | CTTTGATTGTTACGATGGTGGCTGTATTAJ | J = t-butylbenzyl dA |

TABLE 2

SARS-CoV-2 Reverse Primers
Reverse Primers

| Oligo Name | SEQ ID NO: | Sequence | Modifications |
|---|---|---|---|
| D69-70_21690_R | 7 | ACCATCATTAAATGGTAGGACAGGGTTJ | J = t-butylbenzyl dA |
| D69-70_21859R | 8 | GTTAGACTTCTCAGTGGAAGCAAAATAAACJ | J = t-butylbenzyl dA |

TABLE 2-continued

| SARS-CoV-2 Reverse Primers<br>Reverse Primers | | | |
|---|---|---|---|
| Oligo Name | SEQ ID NO: | Sequence | Modifications |
| E484K_23004R | 9 | ACCAACACCATTAGTGGGTTGGAJ | J = t-butylbenzyl dA |
| N501Y_23124AR | 10 | GGTGCATGTAGAAGTTCAAAAGAAAGTACTACTJ | J = t-butylbenzyl dA |
| N501Y_23007_R | 11 | GCTGGTGCATGTAGAAGTTCAAAAGAJ | J = t-butylbenzyl dA |
| Y144_R | 12 | CAATTATTCGCACTAGAATAAACTCTGAACTCJ | J = t-butylbenzyl dA |
| K417_N439_L452_R1 | 13 | GCCTGATAGATTTCAGTTGAAATATCTCTCTCAJ | J = t-butylbenzyl dA |
| K417_N439_L452_R2 | 14 | CGGCCTGATAGATTTCAGTTGAAATATCTJ | J = t-butylbenzyl dA |
| NCOV-1R.A | 15 | AGTGCATCTTGATCCTCATAACTCJ | J = t-butylbenzyl dA |

TABLE 3

| SARS-CoV-2 Probes<br>Probes | | | |
|---|---|---|---|
| Oligo Name | SEQ ID NO: | Sequence | Modifications |
| D69-70-2_PRB | 16 | <JA270>TTCCATGCTATC<BHQ2>TCTGGGACCAATGGTACTAAGAGG<SpcC3> | JA270 = dye<br>BHQ2 = quencher<br>SpcC3 = terminator |
| D69-70_WT1_PRB | 26 | <FAM>TCCATGC<BHQ2>TATACATGTCTCTGGGACCAATGGTACTAAG<SpcC3> | FAM = dye<br>BHQ2 = quencher<br>SpcC3 = terminator |
| D69-70-2_PRB_SHT | 17 | <JA270>TTCCATGCTATC<BHQ2>TCTGGGACCAATGGTAC<SpcC3> | JA270 = dye<br>BHQ2 = quencher<br>SpcC3 = terminator |
| E484K_ML_PRB1 | 18 | <Coum>TGT<D_LNA_T><D_LNA_A><D_LNA_A>AG<BHQ2>GTTTTAATTGTTACTTTCCTTTACAATCATATGGTTTCC<SpcC3> | Coum = dye<br><D_LNA> = D-LNA<br>BHQ2 = quencher<br>SpcC3 = terminator |
| E484K_WT2L_PRB2 | 27 | <FAM>TGT<D_LNA_T><D_LNA_G><D_LNA_A>AG<BHQ2>GTTTTAATTGTTACTTTCCTTTACAATCATATGG<SpcC3> | FAM = dye<br><D_LNA> = D-LNA<br>BHQ2 = quencher<br>SpcC3 = terminator |
| N501Y_HEX_PRB1 | 19 | <HEX>CAC<D_LNA_T><D_LNA_T><D_LNA_A>T<BHQ2>GGTGTTGGTTACCAACCATACAG<SpcC3> | HEX = dye<br><D_LNA> = D-LNA<br>BHQ2 = quencher<br>SpcC3 = terminator |
| N501Y-WT_PRB | 28 | <FAM>CAC<D_LNA_T><D_LNA_A><D_LNA_A>T<BHQ2>GGTGTTGGTTACCAACCATACAG<SpcC3> | FAM = dye<br><D_LNA> = D-LNA<br>BHQ2 = quencher<br>SpcC3 = terminator |
| E484K_ML_FAM1 | 20 | <FAM>TGT<D_LNA_T><D_LNA_A><D_LNA_A>AG<BHQ2>GTTTTAATTGTTACTTTCCTTTACAATCATATGGTTTCC<SpcC3> | FAM = dye<br><D_LNA> = D-LNA<br>BHQ2 = quencher<br>SpcC3 = terminator |
| E484K_WT2L_COU1 | 29 | <Coum>TGT<D_LNA_T><D_LNA_G><D_LNA_A>AG<BHQ2>GTTTTAATTGTTACTTTCCTTTACAATCATATGG<SpcC3> | Coum = dye<br><D_LNA> = D-LNA<br>BHQ2 = quencher<br>SpcC3 = terminator |

TABLE 3-continued

SARS-CoV-2 Probes
Probes

| Oligo Name | SEQ ID NO: | Sequence | Modifications |
|---|---|---|---|
| N501Y-WT_COU1 | 30 | <Coum>TGT<D_LNA_T><D_LNA_G><br><D_LNA_A>AG<BHQ2>GTTTTAA<br>TTGTTACTTTCCTTTACAATCATA<br>TGG<SpcC3> | Coum = dye<br><D_LNA> = D-LNA<br>BHQ2 = quencher<br>SpcC3 = terminator |
| Y144_PRB | 21 | <FAM>TTTGGGTG<BHQ2>TTTAC<br>CACAAAAACAACAAAAGTTGGAT<br>GG<SpcC3> | FAM = dye<br>BHQ2 = quencher<br>SpcC3 = terminator |
| K417N_wt8c | 31 | <FAM>TGGAAAGATT<BHQ2>GCT<br>GA<D_LNA_T><D_LNA_T>ATAA<br><D_LNA_T><D_LNA_T>ATAAA<br><D_LNA_T><D_LNA_T>ACCAGATG<br><SpcC3> | FAM = dye<br><D_LNA> = D-LNA<br>BHQ2 = quencher<br>SpcC3 = terminator |
| K417N_wt8a1 | 32 | <FAM>TGGAA<D_LNA_A><D_LNA_G><br><D_LNA_A>TT<BHQ2>GCTGA<br><D_LNA_T><D_LNA_T>ATAATTA<br>TAAATTACCAGATG<SpcC3> | FAM = dye<br><D_LNA> = D-LNA<br>BHQ2 = quencher<br>SpcC3 = terminator |
| K417N4d | 22 | <Coum>TGGAAA<D_LNA_T>ATT<br><BHQ2>GCTGA<D_LNA_T><D_LNA_T><br>ATAA<D_LNA_T><D_LNA_T>A<br>TAAA<D_LNA_T><D_LNA_T>ACC<br>AGATG<SpcC3> | Coum = dye<br><D_LNA> = D-LNA<br>BHQ2 = quencher<br>SpcC3 = terminator |
| L452R_wt1-zx1 | 33 | <FAM>TACC<D_LNA_T>G<BHQ2><br>TATAGA<D_LNA_T><D_LNA_T>G<br><D_LNA_T><D_LNA_T>TAGGAAG<br>TCTAATCTCAAAC<SpcC3> | FAM = dye<br><D_LNA> = D-LNA<br>BHQ2 = quencher<br>SpcC3 = terminator |
| L452R2-zx1 | 23 | <Coum>TACCG<BHQ2>GTATAGA<br><D_LNA_T><D_LNA_T>G<D_LNA_T><br>TTAGGAAGTCTAATCTCAAAC<br><SpcC3> | Coum = dye<br><D_LNA> = D-LNA<br>BHQ2 = quencher<br>SpcC3 = terminator |
| K417N_wt8cs_J270 | 34 | <JA270>ACTGGAAAGATT<BHQ2><br>GCTGA<D_LNA_T><D_LNA_T>AT<br>AA<D_LNA_T><D_LNA_T>ATAAA<br><D_LNA_T><D_LNA_T>ACCAGAT<br>G<SpcC3> | JA270 = dye<br><D_LNA> = D-LNA<br>BHQ2 = quencher<br>SpcC3 = terminator |
| K417N4cs_J270 | 24 | <JA270>ACTGGAAA<D_LNA_T>AT<br>T<BHQ2>GCTGA<D_LNA_T><D_LNA_T><br>ATAA<D_LNA_T><D_LNA_T><br>ATAAA<D_LNA_T><D_LNA_T><br>ACCAGATG<SpcC3> | JA270 = dye<br><D_LNA> = D-LNA<br>BHQ2 = quencher<br>SpcC3 = terminator |
| N439K_wte2 | 35 | <FAM>CTA<D_LNA_A><D_LNA_5MeC><br><D_LNA_A>ATC<BHQ2>TTG<br>ATT<D_LNA_5MeC>TAAGGTTGGT<br>GGTAAT<SpcC3> | FAM = dye<br><D_LNA> = D-LNA<br>BHQ2 = quencher<br>5MeC = 2'-OmethylC<br>SpcC3 = terminator |
| N439K_e3mC | 25 | <HEX>CTA<D_LNA_A><D_LNA_A><br><D_LNA_A><D_LNA_A>TC<BHQ2><br>TT<D_LNA_G>ATT<D_LNA_5MeC><br>TAA<D_LNA_G>GTTGGTGGTAA<br>TTAT<SpcC3> | HEX = dye<br><D_LNA> = D-LNA<br>BHQ2 = quencher<br>5MeC = 2'-OmethylC<br>SpcC3 = terminator |
| WUHAN-4P_COU6QC3 | 36 | <Coum>TCATCG<BHQ2>TCAACAA<br>CCTAGACAAATCAGCTGGTTTTC<br><SpcC3> | Coum = dye<br>BHQ2 = quencher<br>SpcC3 = terminator |

TABLE 4

SARS-CoV-2 Blocking Probes
Blocking Probes

| Oligo Name | SEQ ID NO: | Sequence | Modifications |
|---|---|---|---|
| E484K_WT2L_NO_DYE | 37 | TGT<D_LNA_T><D_LNA_G><D_LNA_A> AGGTTTTAATTGTTACTTTCC TTTACAATCATATGG<SpcC3> | <D_LNA> = D-LNA SpcC3 = terminator |
| N501Y-WT_NO_DYE | 38 | CAC<D_LNA_T><D_LNA_A><D_LNA_A> TGGTGTTGGTTACCAACCATACAG<SpcC3> | <D_LNA> = D-LNA SpcC3 = terminator |
| LNAD69-70_WT1_NO_DYE | 39 | TCCATGCTATACATGTCTCTGGGA CCAATGGTACTAAG<SpcC3> | SpcC3 = terminator |

In one embodiment, the above-described sets of SARS-CoV-2 primers and probes are used in order to provide for detection of SARS-CoV-2 variants in a biological sample suspected of containing SARS-CoV-2 variants (Tables 1-4). The sets of primers and probes may comprise or consist of the primers and probes specific for the SARS-CoV-2 nucleic acid sequences, comprising or consisting of the nucleic acid sequences of SEQ ID NOs: 1-5, 7-14, 16-25, and 37-39.

As detailed above, a primer (and/or probe) may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the SARS-CoV-2 target, e.g., nucleic acids encoding alternative portions of SARS-CoV-2 can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length).

In addition to a set of primers, the methods may use one or more probes in order to detect the presence or absence of SARS-CoV-2 variants. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a SARS-CoV-2 (target) nucleic acid. A "probe" can be referred to as a "detection probe" meaning that it detects the target nucleic acid.

In some embodiments, the described SARS-CoV-2 probes can be labeled with at least one fluorescent label. In one embodiment, the SARS-CoV-2 probes can be labeled with a donor fluorescent moiety, e.g., a fluorescent dye, and a corresponding acceptor moiety, e.g., a quencher. In one embodiment, the probe comprises or consists of a fluorescent moiety and the nucleic acid sequences comprise or consist of SEQ ID NOs: 21-26.

Designing oligonucleotides to be used as probes can be performed in a manner similar to the design of primers. Embodiments may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 40 (e.g., 16, 18, 20, 21, 22, 23, 24, or 25) nucleotides in length.

Constructs can include vectors each containing one of SARS-CoV-2 primers and probes nucleic acid molecules. Constructs can be used, for example, as control template nucleic acid molecules. Vectors suitable for use are commercially available and/or produced by recombinant nucleic acid technology methods routine in the art. SARS-CoV-2 nucleic acid molecules can be obtained, for example, by chemical synthesis, direct cloning from SARS-CoV-2, or by nucleic acid amplification.

Constructs suitable for use in the methods typically include, in addition to the SARS-CoV-2 nucleic acid molecules (e.g., a nucleic acid molecule that contains one or more sequences of SEQ ID NOs: 1-5, 7-14, and 16-25), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing SARS-CoV-2 nucleic acid molecules can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described SARS-CoV-2 nucleic acid sequences (e.g., SEQ ID NOs: 1-20). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

The genome of a retrovirus or RNA virus, such as SARS-CoV-2 as well as other flaviviruses, is comprised of a ribonucleic acid, i.e., RNA. In such case, the template nucleic acid, RNA, must first be transcribed into complementary DNA (cDNA) via the action of the enzyme reverse transcriptase. Reverse transcriptases use an RNA template and a short primer complementary to the 3' end of the RNA to direct synthesis of the first strand cDNA, which can then be used directly as a template for polymerase chain reaction.

PCR assays can employ SARS-CoV-2 nucleic acid such as RNA or DNA (cDNA). The template nucleic acid need not be purified; it may be a minor fraction of a complex mixture, such as SARS-CoV-2 nucleic acid contained in human cells. SARS-CoV-2 nucleic acid molecules may be extracted from a biological sample by routine techniques such as those described in *Diagnostic Molecular Microbiology: Principles and Applications* (Persing et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers (e.g., SEQ ID NOs: 1-20) are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 μg denatured template DNA, 50 pmoles of each oligonucleotide primer, 2.5 U of Taq polymerase, and 10% DMSO). The reactions usually contain 150 to 320 μM each of dATP, dCTP, dTTP, dGTP, or one or more analogs thereof.

The newly-synthesized strands form a double-stranded molecule that can be used in the succeeding steps of the reaction. The steps of strand separation, annealing, and elongation can be repeated as often as needed to produce the desired quantity of amplification products corresponding to the target SARS-CoV-2 nucleic acid molecules. The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, an oligonucleotide probe can contain a donor fluorescent moiety (e.g., HEX) and a corresponding quencher (e.g., BlackHole Quenchers™ (BHQ)), which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quenchers™ (BHQ), (Biosearch Technologies, Inc., Novato, Cal.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the SARS-CoV-2 target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a xenon lamp, a fiber optic light source, or other high intensity light source appropriately filtered for excitation in the desired range.

As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Foerster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, helium-cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-diethylamino-3-(4'-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide that contains an amino linker (e.g., C6-amino phosphoramidites available from ABI (Foster City, Calif.) or Glen Research (Sterling, VA)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif.)), or 3'-amino-CPGs that require coupling of a fluorescein-NHS-ester after oligonucleotide synthesis.

Detection of SARS-CoV-2

The present disclosure provides methods for detecting the presence or absence of SARS-CoV-2 variant having a Spike protein mutation (including deletion and insertion) in a biological or non-biological sample. Methods provided avoid problems of sample contamination, false negatives, and false positives. The methods include performing a reverse transcription step and at least one cycling step that includes amplifying a portion of SARS-CoV-2 S gene nucleic acid molecules from a sample using one or more pairs of SARS-CoV-2 primers, and a FRET detecting step. Multiple cycling steps are performed, preferably in a thermocycler. Methods can be performed using the SARS-CoV-2 S gene primers and probes to specifically detect the presence of SARS-CoV-2 S gene mutations, and the detection of the SARS-CoV-2 indicates the presence of SARS-CoV-2 variants in the sample.

As described herein, amplification products can be detected using labeled hybridization probes that take advantage of FRET technology. One FRET format utilizes TaqMan® technology to detect the presence or absence of an amplification product, and hence, the presence or absence of SARS-CoV-2 variants. TaqMan® technology utilizes one single-stranded hybridization probe labeled with, e.g., one fluorescent dye (e.g., HEX) and one quencher (e.g., BHQ), which may or may not be fluorescent. When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of SARS-CoV-2 variants in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of SARS-CoV-2 genomes). If amplification of SARS-CoV-2 target nucleic acid occurs and an amplification product is produced, the step of hybridizing results in a detectable signal based upon FRET between the members of the pair of probes.

Generally, the presence of FRET indicates the presence of SARS-CoV-2 in the sample, and the absence of FRET indicates the absence of SARS-CoV-2 in the sample. Inadequate specimen collection, transportation delays, inappropriate transportation conditions, or use of certain collection swabs (calcium alginate or aluminum shaft) are all conditions that can affect the success and/or accuracy of a test result, however.

Representative biological samples that can be used in practicing the methods include, but are not limited to respiratory specimens (nasopharyngeal and oropharyngeal swabs), urine, fecal specimens, blood specimens, plasma, dermal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release SARS-CoV-2 nucleic acid or in some cases, the biological sample can be contacted directly with the PCR reaction components and the appropriate oligonucleotides.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the SARS-CoV-2 probes from the SARS-CoV-2 amplification products can confirm the presence or absence of SARS-CoV-2 in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the methods. In one embodiment, a LightCycler® instrument is used. The following patent applications describe real-time PCR as used in the LightCycler® technology: WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

One of skill in the art would appreciate that other nucleic acid- or signal-amplification methods may also be employed. Examples of such methods include, without limitation, branched DNA signal amplification, loop-mediated isothermal amplification (LAMP), nucleic acid sequence-based amplification (NASBA), self-sustained sequence replication (3SR), strand displacement amplification (SDA), or smart amplification process version 2 (SMAP 2).

It is understood that the embodiments of the present disclosure are not limited by the configuration of one or more commercially available instruments.

Articles of Manufacture/Kits

Embodiments of the present disclosure further provide for articles of manufacture or kits to detect SARS-CoV-2 variant having a Spike protein mutation. An article of manufacture can include primers and probes used to detect the SARS-CoV-2 S gene target, together with suitable packaging materials. Representative primers and probes for specific detection of SARS-CoV-2 S gene mutations are capable of hybridizing to SARS-CoV-2 target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to SARS-CoV-2 S gene target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the SARS-CoV-2 probes. Examples of suitable FRET donor fluorescent moieties and corresponding acceptor fluorescent moieties are provided above.

Articles of manufacture can also contain a package insert or package label having instructions thereon for using the SARS-CoV-2 primers and probes to detect SARS-CoV-2 variant having a Spike protein mutation in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure will be further described in the following examples, which do not limit the scope of the invention described in the claims.

EXAMPLES

The following examples and figures are provided to aid the understanding of the subject matter, the true scope of which is set forth in the appended claims. It is understood that modifications can be made in the procedures set forth without departing from the spirit of the invention.

Example 1 Assay Description

A real-time Reverse Transcription-Polymerase Chain Reaction (RT-PCR) test was developed on the cobas® 6800/8800 Systems for the qualitative and differentiation of SARS-CoV-2 mutations N501Y, del 69-70 and E484K in e.g., nasal and nasopharyngeal swab specimens from patients with known SARS-COV-2 infection to support the understanding of variant epidemiology 20 for Population Health Management. Mutation specific PCR assays can be used as a reflex test for SARS-COV-2 positive samples to identify known mutations of concern as part of a surveillance strategy for SARS-COV-2 variants. Assays were strategically designed to enable single base mutation detection with hydrolysis (TaqMan®) probes incorporated with Locked Nucleic Acid (LNA) chemistry to increase melting temperature (TM) and to drive specificity for detection of the point mutations, E484K and N501Y. The detection of the 6-base deletion in del 69-70 could be performed with traditional TaqMan® probe. The assay also included three dye-less wildtype (wt) probes for del69-70, E484K and N501Y that serve as blocking oligonucleotide probes. The assay was performed under competitive conditions with both the fluorescently labeled mutant probes and wt dye-less probes present so mismatched probes would be prevented from binding due to stable binding of the exact-match probes. In one embodiment, the blocking oligonucleotide probes are incorporated with LNA to further increase the Tm difference between a perfectly matched and a single-base (or more) mismatched sequence. The test also included as a control, a SARS-COV-2 wildtype-specific ORF1a/b assay using a Coumarin-labeled probe.

Nucleic acid from patient samples and added RNA-Internal Control molecules (same as the existing RNA QS reagent) are simultaneously extracted. Viral nucleic acids are released by addition of proteinase and lysis reagent to the sample. The released nucleic acid binds to the silica surface of the added magnetic glass particles. Unbound substances and impurities, such as denatured proteins, cellular debris and potential PCR inhibitors are removed with subsequent wash reagent steps and purified nucleic acid is eluted from the magnetic glass particles with elution buffer at elevated temperature.

Example 2: Selection of Primer and Probe Oligonucleotides

A master mix contains fluorescently labeled detection probes which are specific for the S gene mutations, E484K, N501Y, del 69-70 and also the wild-type ORF 1a/b gene. An RNA Internal Control detection probe was also labeled with the Cy5.5 dye that act as a reporter. Each probe also contained a second dye which acts as a quencher. PCR Primers for amplifying the region of interest were designed to the target regions. Thus, studies were initiated with a single well assay design that detected SARS-CoV-2 variants containing S gene mutations using: (i) The non-structural Open Reading Frame (ORF1a/b) in the genome of the SARS-CoV-2 in the coumarin channel; (ii) The S gene E484K mutation in the FAM channel; (iii) The S gene N501K mutation in the HEX channel; (iv) The S gene 69-70 deletion in the JA270 channel. A bioinformatics analysis of the various assays that could be multiplexed with RNA Internal Control oligonucleotides that are used for detection of the process control was done to screen initial assays for performance. Competing unlabeled wildtype oligonucleotides (i.e. blocking probes) were included in the master mix for E484, N501, wt 69-70 in order to increase assay specificity. Select combination set of primers and probes are shown in Table 5.

TABLE 5

| SARS-CoV-2 Variant Test Configuration | | | | |
|---|---|---|---|---|
| Assay Name | Dye Channel | Oligo Name | SEQ ID NO: | Blocking Probe |
| E484K | FAM | E484K_23004F | 2 | E484K_WT2L_NO_DYE |
| | | N501Y_23124AR | 10 | SEQ ID NO: 37 |
| | | E484K_ML_FAM1 | 20 | |
| N501Y | HEX | E484K_23004F | 2 | N501Y-WT_NO_DYE |
| | | N501Y_23124aR | 10 | SEQ ID NO: 38 |
| | | N501Y_HEX_PRB1 | 19 | |
| del 69-70 | JA270 | D69-70_21690_F | 1 | D69-70_WT1_NO_DYE |
| | | D69-70_21859R | 7 | SEQ ID NO: 39 |
| | | D69-70-2_PRB_SHT | 17 | |
| Orf1a/b | Coumarin | NCOV-1-FN1.A | 6 | N/A |
| | | NCOV-1R.A | 15 | |
| | | WUHAN-4P_COU6QC3 | 36 | |

Example 3: PCR Assay Reagents and Conditions

Real-time PCR detection of SARS-CoV-2 (both wild type and variants) was performed using the Cobas® 6800/8800 systems platforms (Roche Molecular Systems, Inc., Pleasanton, CA). The final concentrations of the amplification reagents are shown below:

TABLE 6

| PCR Amplification Reagents | | |
|---|---|---|
| Master Mix Component | Final Conc (50 uL) | |
| DMSO | 0-5.4 | % |
| NaN3 | 0.027-0.030 | % |
| Potassium acetate | 120.0 | mM |
| Glycerol | 3.0 | % |
| Tween 20 | 0.015 | % |
| EDTA | 43.9 | uM |
| Tricine | 60.0 | mM |
| NTQ21-46A Aptamer | 0.222 | uM |
| UNG Enzyme | 5.0-10.0 | U |
| Z05-D Polymerase | 30.0-45.0 | U |
| dATP | 400.0 | uM |
| dCTP | 400.0 | uM |
| dGTP | 400.0 | uM |
| dUTP | 800.0 | uM |
| Forward primer oligonucleotides | 0.30-0.40 | µM |
| Reverse primer oligonucleotides | 0.30-0.40 | µM |
| Probe oligonucleotides | 0.10 | µM |

The following table shows the typical thermoprofile used for PCR amplification reaction:

TABLE 7

| PCR Thermoprofile | | | | | | |
|---|---|---|---|---|---|---|
| Program Name | Target (° C.) | Acquisition Mode | Hold (hh:mm:ss) | Ramp Rate (° C./s) | Cycles | Analysis Mode |
| Pre-PCR | 50 | None | 00:02:00 | 4.4 | 1 | None |
| | 94 | None | 00:00:05 | 4.4 | | |
| | 55 | None | 00:02:00 | 2.2 | | |
| | 60 | None | 00:06:00 | 4.4 | | |
| | 65 | None | 00:04:00 | 4.4 | | |
| 1st Measurement | 95 | None | 00:00:05 | 4.4 | 5 | Quantification |
| | 55 | Single | 00:00:30 | 2.2 | | |
| 2nd Measurment | 91 | None | 00:00:05 | 4.4 | 45 | Quantification |
| | 58 | Single | 00:00:25 | 2.2 | | |
| Cooling | 40 | None | 00:02:00 | 2.2 | 1 | None |

The Pre-PCR program comprised initial denaturing and incubation at 55° C., 60° C. and 65° C. for reverse transcription of RNA templates. Incubating at three temperatures combines the advantageous effects that at lower temperatures slightly mismatched target sequences (such as genetic variants of an organism) are also transcribed, while at higher temperatures the formation of RNA secondary structures is suppressed, thus leading to a more efficient transcription. PCR cycling was divided into two measurements, wherein both measurements apply a one-step setup (combining annealing and extension). The first 5 cycles at 55° C. allow for an increased inclusivity by pre-amplifying slightly mismatched target sequences, whereas the 45 cycles of the second measurement provide for an increased specificity by using an annealing/extension temperature of 58° C.

Example 4: Performance Assessment

Assessment of components, workflows and assay reagents for the SARS-CoV-2 variant test were performed using the Cobas® 6800 reagents. Linearized recombinant plasmids were tested with the assay oligonucleotides to assess performance. In vitro transcripts were also generated to evaluate performance of the assays using synthetic RNA. Nucleic acid quantitation was done using Qubit with DNA and RNA standards. Plasmid DNA and transcripts were serially diluted in MultiPrep Specimen Diluent Buffer (also known as Bulk Generic Specimen Diluent) and used in assay performance studies. Internal control oligonucleotides (generic internal control, GIC) were included in the evaluations with both linearized DNA and RNA transcripts. Experiments were conducted on the Analytical Cycler in the Cobas® 6800 System. Nasopharyngeal (NSP) samples were obtained from patients exhibiting upper respiratory symptoms using flocculated swabs and collected in Universal Viral Transport Medium (3 mL). A modified sample preparation workflow (Process and Elute, PnE) was used on the Cobas® 6800 System wherein either 300 or 400 μL of NSP sample was processed to prepare nucleic acid eluates. These eluates contain the gIC armored RNA (QS RNA Control) that follow the same NSP sample preparation process on the Cobas® 6800 and serves as the internal sample processing control. Eluates were then used in studies with the SARS-CoV-2 assays with amplification and detection on the LC480 and/or the Cobas® 6800 analytical cycler.

Figure 2:
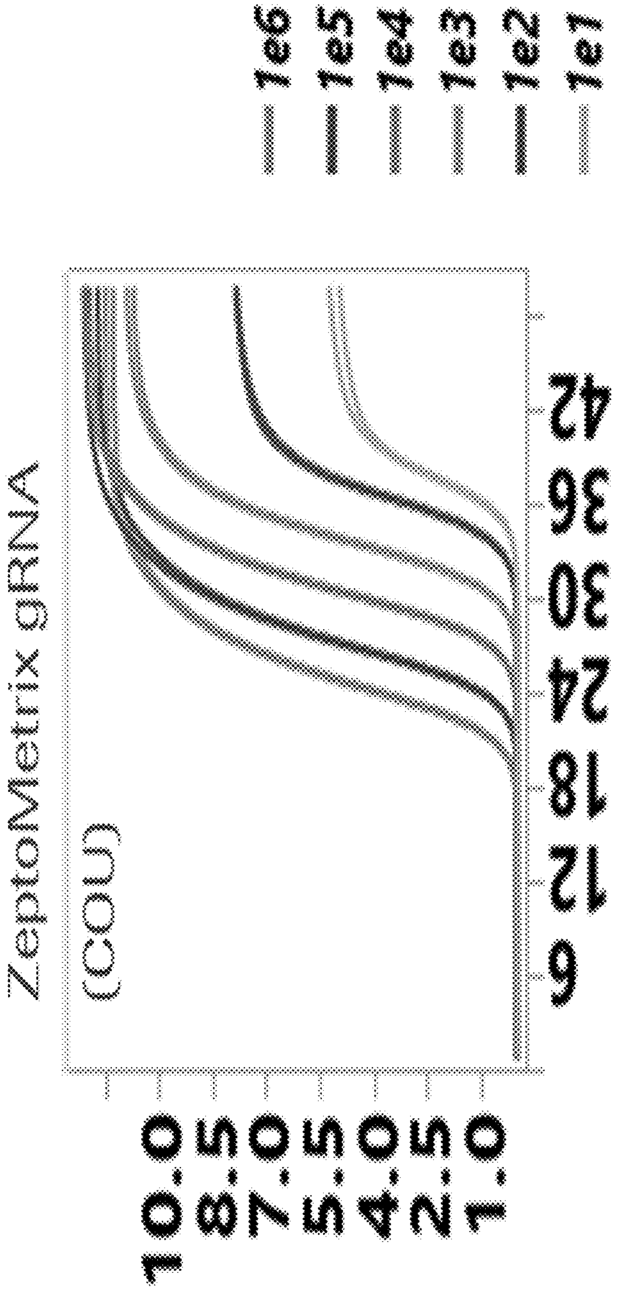
FIG. 2 shows the growth curves generated from the SARS-CoV-2 Variant Test described in Example 4 using Zeptometrix wild type SARS-CoV-2 genomic RNA at the indicated levels in a multiplex PCR test with detection at the Coumarin channel.
Figure 3:
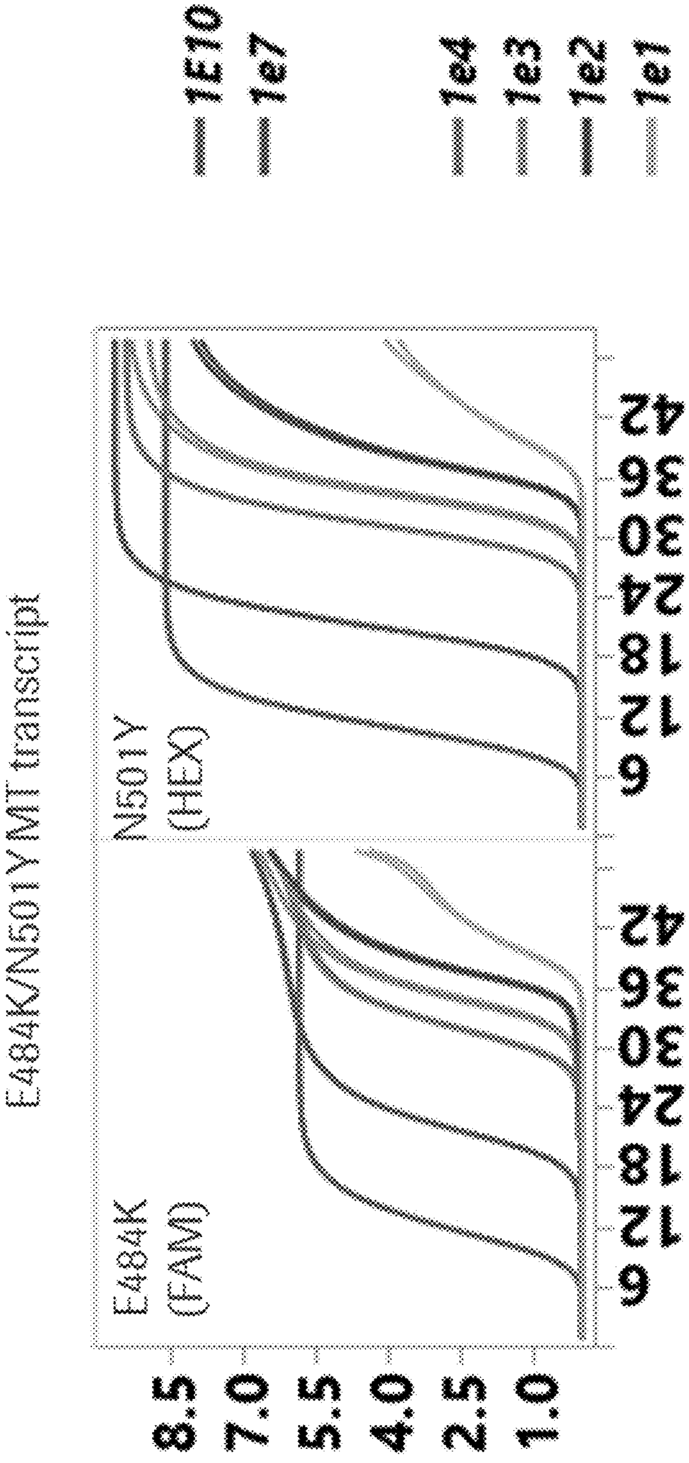
FIG. 3 shows the growth curves generated from the SARS-CoV-2 Variant Test described in Example 4 using a mutant transcript that contained both E484K and N501Y mutations at the indicated levels in a multiplex PCR test with detection at the FAM channel (left) and at the HEX channel (right).
Figure 4:
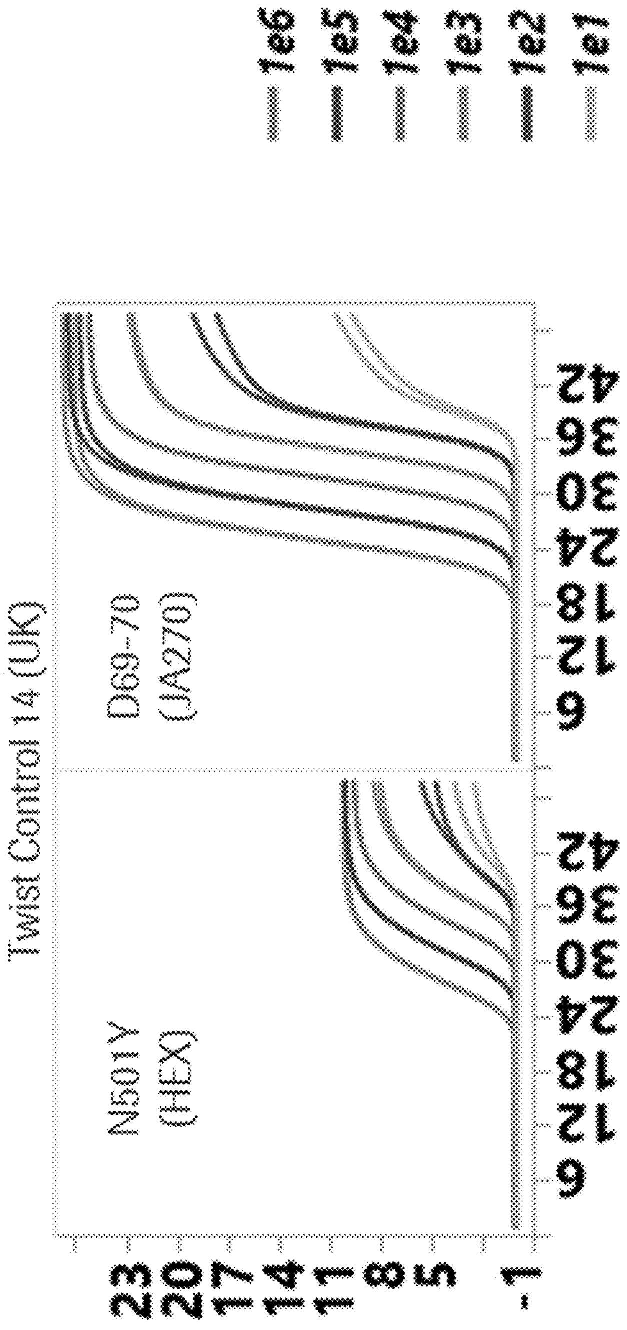
FIG. 4 shows the growth curves generated from the SARS-CoV-2 Variant Test described in Example 4 using a Twist synthetic control transcript carrying both the N501Y mutation and the 69-70 deletion at the indicated levels in a multiplex PCR test with detection at the HEX channel (left) and at the JA270 channel (right).

Multiplex PCR assays were then performed in which the primers and probe oligonucleotides described in TABLE 5 were tested in a single reaction. Test samples (n=2) included Zeptometrix SARS-CoV-2 wild type genomic RNA tested at concentrations of 1e6-1e1 copies/PCR, a mutant transcript that contained both E484K and N501Y mutations, tested at concentrations of 1e10-1e1 copies/PCR, and a Twist synthetic control transcript carrying both the N501Y mutation and the 69-70 deletion, tested at concentrations of 1e6-1e1 copies/PCR. All experiments were performed in contrived NPS and the results of these tests are shown in FIGS. 2, 3 and 4. The data indicate robust growth curves and PCR efficiency over a wide dynamic range with transcripts detected down to 10 copies per PCR reaction for all targets.

Example 5: Determination of Analytical Sensitivity (Limit of Detection)

For determination of analytical sensitivity, six SARS-CoV-2 virus stocks were used. Two isolates each were prepared at the University of Zurich (isolate UZ1: P.2 lineage, clade 20B with E484K; isolate UZ2: B.1 lineage, clade 20A with N501Y), and at the University of Frankfurt (isolate UF1: B.1.351 lineage, clade 20H/501Y.V2 with E484K and N501Y; and isolate UF2: B.1.1.7 lineage, clade 20I/501Y.V1 with N501Y and del 69/70). Labor Berlin used two isolates which were kindly provided by the National Consultation Laboratory for Coronaviruses at the Institute of Virology, Medical University, Charité, Berlin ((isolate LB1: B.1.351 lineage, clade 20H/501Y.V2 with E484K and N501Y; and isolate LB2: B.1.1.7 lineage, clade 20I/501Y.V1 with N501Y and del 69/70).

The titers of virus stocks were determined using the Cobas® SARS-CoV-2 assay for use on the Cobas® 6800/8800 system, which reports a cycle threshold (Ct) value. The First World Health Organization (WHO) International Standard for SARS-CoV-2 ribonucleic acid (RNA; NIBSC National Institute for Biological Standards and Control code 20/146) was also tested in this assay at two different concentrations (3.7 and 5.7 log IU/ml), allowing conversion of Ct for unknown samples to international units (IU) based on the linear regression of the standard curve (log 10 IU/mL=12.66-0.297*Ct). Four to seven dilutions of each of the six different virus isolates were prepared in CPM (Cobas® PCR Media) or a UTM-based simulated matrix (UTM, 50,000 human peripheral blood monocytes cells/mL, 0.05% mucin) to generate panels that included at least four concentrations: ~3-fold, equal to, 0.3-fold, and 0.1-fold the expected limit of detection (LoD). Each panel member was tested in 21 replicates. LoD was determined using hit rate analysis (the concentration yielding at least 95% positive results) and reported in IU/mL.

The lowest virus concentrations tested that gave at least 95% positive results for each locus, as well as the corresponding mean cycle threshold values for the SCI control, are shown in TABLE 8. The limit of detection (LoD) determined by this method for E484K was between 180 and 620 IU/mL for the three different isolates tested. For N501Y, the LoD was between 270 and 720 IU/mL (five isolates), while for the deletion of codons 69 and 70, it was 80 or 92 IU/mL. The LoD for the SCI positive control target was between 18 and 80 IU/mL.

TABLE 8

Assay Sensitivity (Limit of Detection)

| | | | | Limit of Detection[a] | | | | |
|---|---|---|---|---|---|---|---|---|
| | | | | SCI | | E484K | N501Y | del 69-70 |
| Isolate | Lineage | Clade | Spike genotype | IU/mL | Mean Ct | IU/mL | IU/mL | IU/mL |
| UZ1 | P.2 | 20B | E484K | 23 | 37.7 | 620 | — | — |
| UZ2 | B.1 | 20A | N501Y | 30 | 37.4 | — | 270 | — |
| UF1 | B.1.351 | 20H/501Y.V2 | E484K, N501Y | 64 | 36.7 | 190 | 580 | — |
| UF2 | B.1.1.7 | 20I/501Y.V1 | del 69/70, N501Y | 80 | 37.3 | — | 720 | 80 |
| LB1 | B.1.351 | 20H/501Y.V2 | E484K, N501Y | 18 | 38.1 | 180 | 550 | — |
| LB2 | B.1.1.7 | 20I/501Y.V1 | del 69/70, N501Y | 28 | 37.6 | — | 280 | 92 |

[a]the lowest concentration tested that resulted in ≥95% positive results is shown
SCI: sample check indicator
Ct: cycle threshold

Example 6: Determination of Accuracy Using Clinical Specimens

To determine the accuracy of the SARS-CoV-2 variant test, specimens containing SARS-CoV-2 with or without one or more of the three target loci were tested at four sites. The presence or absence of mutations was established by sequencing of S using standard Sanger-based method (University of Zurich) or next-generation methods (Labor Berlin, University Hospital of Regensburg and Bioscentia, Ingelheim; see Supplemental Methods). A total of 273 isolates were included. The standard Sanger-based method used at the University of Zurich does not cover the deletion at codons 69-70, so these samples were excluded from the analysis for that locus. All samples were RT-PCR positive using a variety of commercial or laboratory-developed tests. A variety of specimen types including nasal, nasopharyngeal and oropharyngeal swabs, broncheo-alveolar lavage, tracheal secretions, and respiratory wash in diverse media (water, saline, universal transport medium, cobas PCR medium, etc.) were included (TABLE 9).

TABLE 9

| Specimens Used For Accuracy Evaluation | | | | | |
|---|---|---|---|---|---|
| | specimen collection site | | | | |
| specimen type | University of Zurich | Labor Berlin | University Hospital Regensburg | Bioscentia Ingelheim | Total |
| broncheo-alveolar lavage | | | 2 | | 2 |
| processed sputum | | | 1 | | 1 |
| NS, NPS, or OPS[a] | 15 | 148 | 16 | 44 | 223 |
| throat irrigation fluid | | | 40 | | 40 |
| tracheal secretion | | | 7 | | 7 |
| Total | 15 | 148 | 66 | 44 | 273 |

[a]NS: nasal swab;
NPS: nasopharyngeal swab;
OPS: oropharyngeal swab

The SCI control reaction for all 273 isolates was positive, indicating the presence of viral RNA in the sample. A total of 20 specimens with E484K present according to sequencing were tested (TABLE 10); all were reactive with the E484K probe (sensitivity: 100%). Conversely, reactivity with E484K was absent in 252 specimens with no substitution at position 484 (specificity: 100%). One sample was missing sequence data for position 484. Similar results were obtained for N501Y (108 specimens with the substitution, 164 without; one sample missing sequence data) and the deletion of codons 69 and 70 (99 specimens with the deletion, 157 without; sequence data for this region was missing for 17 samples) and are summarized in TABLE 10. No false positive or false negative results were observed.

TABLE 10

| Assay Accuracy | | | | |
|---|---|---|---|---|
| Target | Result | Mutation present | Mutation absent | Overall agreement % (95% CI) |
| E484K[a] | positive | 20 | 0 | 100 (98.7-100) |
| | negative | 0 | 252 | |
| N501Y[a] | positive | 108 | 0 | 100 (98.7-100) |
| | negative | 0 | 164 | |
| Del 69-70[b] | positive | 99 | 0 | 100 (98.6-100) |
| | negative | 0 | 157 | |

[a]one sample was missing sequence data for positions 484 and 501
[b]17 samples were missing sequence data for positions 69-70

Example 7: Determination of Analytical Specificity (Interfering Organisms)

Specificity was assessed using contrived samples containing one of 17 different viruses (target concentration: 105 units per mL in UTM-based simulated matrix), eight bacteria (106 units per mL) or *pneumocystis jirovecii* (106 units per mL). The 17 viruses tested were adenovirus, enterovirus, human coronavirus 229E, HKU1, NL63, and OC43, human metapneumovirus, influenza A and B virus, MERS-coronavirus, Parainfluenza virus 1, 2, 3 and 4, respiratory syncytial virus, human rhinovirus, and SARS-coronavirus. The eight bacteria were *Bordetella pertussis, Chlamydia pneumoniae, Haemophilus influenzae, Legionella pneumophila, Mycobacterium tuberculosis, Mycoplasma pneumoniae, Streptococcus pyogenes, Streptococcus pneumoniae*. No signal was observed for the SCI or any of the targeted mutations with any of the specimens containing potentially cross-reacting organisms.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed:

1. A multiplex method for detecting a SARS-CoV-2 variant having a Spike protein mutation in a biological sample comprising:

performing an amplifying step comprising contacting the sample with at least two sets of primers to produce first and second amplification products if the SARS-CoV-2 nucleic acid is present in the sample;

performing a hybridizing step comprising contacting the amplification products with at least three detectable probes hybridizing to the first and second amplification products produced by the at least two sets of primers; and detecting the presence of at least one of the first and second amplification products, wherein the presence of the at least one amplification product is indicative of the presence of the SARS-CoV-2 variant in the sample; and wherein a first set of primers comprises a forward primer comprising or consisting of an oligonucleotide sequence of SEQ ID NO: 1, and a reverse primer comprising or consisting of an oligonucleotide of SEQ ID NOs: 7 or 8; and a second set of primers comprises a forward primer comprising or consisting of an oligonucleotide sequence of SEQ ID NO: 2, and a reverse primer comprising or consisting of an oligonucleotide sequence of SEQ ID NOs: 9, 10 or 11; and wherein a first detectable probe hybridizing to the first amplification product produced by the first set of primers comprises or consists of an oligonucleotide sequence selected from the group consisting of SEQ ID NOs: 16-17, or a complement thereof; wherein a second detectable probe hybridizing to the second amplification product produced by the second set of primers comprises or consists of an oligonucleotide sequence of SEQ ID NO: 19, or a complement thereof; and wherein a third detectable probe hybridizing to the second amplification product produced by the second set of primers comprises or consists of the oligonucleotide sequence of SEQ ID NO: 20, or a complement thereof; and wherein the Spike protein mutation is selected from a 69-70 deletion (del 69-70), a N501Y mutation, or a E484K mutation, or combinations thereof.

2. The method of claim 1, wherein the hybridizing step or both the amplifying step and the hybridizing step are performed in the presence of one or more blocking oligonucleotide probes; wherein the one or more blocking probes comprise or consist of the oligonucleotide sequence of SEQ ID NOs: 37, 38 or 39, or any combinations thereof.

3. The method of claim 1, further comprising providing a set of primers that amplifies specific nucleic acid sequences from the non-structural Open Reading Frame (ORF1a/b) gene of SARS-CoV-2 and a detectable probe that hybridizes to and detects an ORF1a/b amplification product generated by the set of primers.

4. The method of claim 3, wherein the set of primers that amplifies the ORF1a/b gene comprises a forward primer comprising or consisting of an oligonucleotide sequence of SEQ ID NO: 6 and a reverse primer comprising or consisting of an oligonucleotide sequence of SEQ ID NO: 15; and the detectable probe comprises or consists of an oligonucleotide sequence of SEQ ID NO: 36, or a complement thereof.

5. The method of claim 1, wherein the first set of primers for amplification of the SARS-CoV-2 nucleic acid comprises the forward primer comprising or consisting of the oligonucleotide sequence of SEQ ID NO: 1, and the reverse primer comprising or consisting of the oligonucleotide sequence of SEQ ID NO: 8, and wherein the first detectable probe comprises or consists of the oligonucleotide sequence of SEQ ID NO: 17, or a complement thereof.

6. The method of claim 1, wherein the second set of primers for amplification of the SARS-CoV-2 nucleic acid comprises the forward primer comprising or consisting of the oligonucleotide sequence of SEQ ID NO: 2, and the reverse primer comprising or consisting of the oligonucleotide sequence of SEQ ID NO: 10.

7. A multiplex method for detecting at least one SARS-CoV-2 variant having a Spike protein mutation in a biological sample comprising:

performing an amplifying step comprising contacting the sample with at least two sets of primers to produce first and second amplification products if the SARS-CoV-2 nucleic acid is present in the sample;

performing a hybridizing step comprising contacting the amplification products with at least three detectable probes hybridizing to the first and second amplification products produced by the at least two sets of primers; and detecting the presence of at least one of the first and second amplification products, wherein the presence of the at least one amplification product is indicative of the presence of the SARS-CoV-2 variant in the sample, wherein a first set of primers comprises a forward primer consisting of an oligonucleotide sequence of SEQ ID NO: 1, and a reverse primer consisting of an oligonucleotide of SEQ ID NO: 7, or 8 wherein a second set of primers comprises a forward primer consisting of an oligonucleotide sequence of SEQ ID NO: 2, and a reverse primer consisting of an oligonucleotide of SEQ ID NO: 10, wherein a first detectable probe hybridizing to the first amplification product produced by the first set of primers consists of an oligonucleotide sequence selected from SEQ ID NO: 17, or a complement thereof, wherein a second detectable probe hybridizing to the second amplification product produced by the second set of primers consists of an oligonucleotide sequence selected from SEQ ID NO: 19, or a complement thereof, wherein a third detectable probe hybridizing to the second amplification product produced by the second set of primers consists of an oligonucleotide sequence selected from SEQ ID NO: 20, or a complement thereof, and wherein the Spike protein mutation is a 69-70 deletion (del 69-70), a N501Y mutation, or a E484K mutation, or combinations thereof.

8. The method of claim 1, wherein the hybridizing step or both the amplifying step and the hybridizing step are performed in the presence of at least one blocking oligonucleotide probe, the at least one blocking oligonucleotide probe comprising or consisting of the oligonucleotide sequence of SEQ ID NO: 39.

* * * * *

SEQUENCE LISTING

```
<160> NUMBER OF SEQ ID NOS: 39

<210> SEQ ID NO 1
<211> LENGTH: 28
<212> TYPE: DNA
<213> ORGANISM: Artificial Sequence
<220> FEATURE:
<223> OTHER INFORMATION: Forward Primer D69-70_21690_F
<220> FEATURE:
<221> NAME/KEY: modified_base
<222> LOCATION: (28)..(28)
<223> OTHER INFORMATION: t-butylbenzyl dA

<400> SEQUENCE: 1

tcagatcctc agttttacat tcaactca                                        28


<210> SEQ ID NO 2
<211> LENGTH: 20
<212> TYPE: DNA
<213> ORGANISM: Artificial Sequence
```

<220> FEATURE:
<223> OTHER INFORMATION: Forward Primer E484K_23004F
<220> FEATURE:
<221> NAME/KEY: modified_base
<222> LOCATION: (20)..(20)
<223> OTHER INFORMATION: t-butylbenzyl dA

<400> SEQUENCE: 2
gccggtagca caccttgtaa 20

<210> SEQ ID NO 3
<211> LENGTH: 27
<212> TYPE: DNA
<213> ORGANISM: Artificial Sequence
<220> FEATURE:
<223> OTHER INFORMATION: Forward Primer Y144_F
<220> FEATURE:
<221> NAME/KEY: modified_base
<222> LOCATION: (27)..(27)
<223> OTHER INFORMATION: t-butylbenzyl dA

<400> SEQUENCE: 3
gaagacccag tccctactta ttgttaa 27

<210> SEQ ID NO 4
<211> LENGTH: 22
<212> TYPE: DNA
<213> ORGANISM: Artificial Sequence
<220> FEATURE:
<223> OTHER INFORMATION: Forward Primer K417_N439_L452_F1
<220> FEATURE:
<221> NAME/KEY: modified_base
<222> LOCATION: (22)..(22)
<223> OTHER INFORMATION: t-butylbenzyl dA

<400> SEQUENCE: 4
tgaagtcaga caaatcgctc ca 22

<210> SEQ ID NO 5
<211> LENGTH: 19
<212> TYPE: DNA
<213> ORGANISM: Artificial Sequence
<220> FEATURE:
<223> OTHER INFORMATION: Forward Primer K417_N439_L452_F2
<220> FEATURE:
<221> NAME/KEY: modified_base
<222> LOCATION: (19)..(19)
<223> OTHER INFORMATION: t-butylbenzyl dA

<400> SEQUENCE: 5
acaaatcgct ccagggcaa 19

<210> SEQ ID NO 6
<211> LENGTH: 30
<212> TYPE: DNA
<213> ORGANISM: Artificial Sequence
<220> FEATURE:
<223> OTHER INFORMATION: Forward Primer NCOV-1-FN1.A
<220> FEATURE:
<221> NAME/KEY: modified_base
<222> LOCATION: (30)..(30)
<223> OTHER INFORMATION: t-butylbenzyl dA

<400> SEQUENCE: 6
ctttgattgt tacgatggtg gctgtattaa 30

<210> SEQ ID NO 7
<211> LENGTH: 28
<212> TYPE: DNA

<213> ORGANISM: Artificial Sequence
<220> FEATURE:
<223> OTHER INFORMATION: Reverse Primer D69-70_21690_R
<220> FEATURE:
<221> NAME/KEY: modified_base
<222> LOCATION: (28)..(28)
<223> OTHER INFORMATION: t-butylbenzyl dA

<400> SEQUENCE: 7
accatcatta aatggtagga cagggtta 28

<210> SEQ ID NO 8
<211> LENGTH: 31
<212> TYPE: DNA
<213> ORGANISM: Artificial Sequence
<220> FEATURE:
<223> OTHER INFORMATION: Reverse Primer D69-70_21859R
<220> FEATURE:
<221> NAME/KEY: modified_base
<222> LOCATION: (31)..(31)
<223> OTHER INFORMATION: t-butylbenzyl dA

<400> SEQUENCE: 8
gttagacttc tcagtggaag caaaataaac a 31

<210> SEQ ID NO 9
<211> LENGTH: 24
<212> TYPE: DNA
<213> ORGANISM: Artificial Sequence
<220> FEATURE:
<223> OTHER INFORMATION: Reverse Primer E484K_23004R
<220> FEATURE:
<221> NAME/KEY: modified_base
<222> LOCATION: (24)..(24)
<223> OTHER INFORMATION: t-butylbenzyl dA

<400> SEQUENCE: 9
accaacacca ttagtgggtt ggaa 24

<210> SEQ ID NO 10
<211> LENGTH: 34
<212> TYPE: DNA
<213> ORGANISM: Artificial Sequence
<220> FEATURE:
<223> OTHER INFORMATION: Reverse Primer N501Y_23124AR
<220> FEATURE:
<221> NAME/KEY: modified_base
<222> LOCATION: (34)..(34)
<223> OTHER INFORMATION: t-butylbenzyl dA

<400> SEQUENCE: 10
ggtgcatgta gaagttcaaa agaaagtact acta 34

<210> SEQ ID NO 11
<211> LENGTH: 27
<212> TYPE: DNA
<213> ORGANISM: Artificial Sequence
<220> FEATURE:
<223> OTHER INFORMATION: Reverse Primer N501Y_23007_R
<220> FEATURE:
<221> NAME/KEY: modified_base
<222> LOCATION: (27)..(27)
<223> OTHER INFORMATION: t-butylbenzyl dA

<400> SEQUENCE: 11
gctggtgcat gtagaagttc aaaagaa 27

<210> SEQ ID NO 12
<211> LENGTH: 33

<212> TYPE: DNA
<213> ORGANISM: Artificial Sequence
<220> FEATURE:
<223> OTHER INFORMATION: Reverse Primer Y144_R
<220> FEATURE:
<221> NAME/KEY: modified_base
<222> LOCATION: (33)..(33)
<223> OTHER INFORMATION: t-butylbenzyl dA

<400> SEQUENCE: 12
caattattcg cactagaata aactctgaac tca 33

<210> SEQ ID NO 13
<211> LENGTH: 33
<212> TYPE: DNA
<213> ORGANISM: Artificial Sequence
<220> FEATURE:
<223> OTHER INFORMATION: Reverse Primer K417_N439_L452_R1
<220> FEATURE:
<221> NAME/KEY: modified_base
<222> LOCATION: (33)..(33)
<223> OTHER INFORMATION: t-butylbenzyl dA

<400> SEQUENCE: 13
gcctgataga tttcagttga aatatctctc tca 33

<210> SEQ ID NO 14
<211> LENGTH: 30
<212> TYPE: DNA
<213> ORGANISM: Artificial Sequence
<220> FEATURE:
<223> OTHER INFORMATION: Reverse Primer K417_N439_L452_R2
<220> FEATURE:
<221> NAME/KEY: modified_base
<222> LOCATION: (30)..(30)
<223> OTHER INFORMATION: t-butylbenzyl dA

<400> SEQUENCE: 14
cggcctgata gatttcagtt gaaatatcta 30

<210> SEQ ID NO 15
<211> LENGTH: 25
<212> TYPE: DNA
<213> ORGANISM: Artificial Sequence
<220> FEATURE:
<223> OTHER INFORMATION: Reverse Primer NCOV-1R.A
<220> FEATURE:
<221> NAME/KEY: modified_base
<222> LOCATION: (25)..(25)
<223> OTHER INFORMATION: t-butylbenzyl dA

<400> SEQUENCE: 15
agtgcatctt gatcctcata actca 25

<210> SEQ ID NO 16
<211> LENGTH: 36
<212> TYPE: DNA
<213> ORGANISM: Artificial Sequence
<220> FEATURE:
<223> OTHER INFORMATION: Probe D69-70-2_PRB
<220> FEATURE:
<221> NAME/KEY: misc_feature
<223> OTHER INFORMATION: 5' JA270
<220> FEATURE:
<221> NAME/KEY: misc_feature
<223> OTHER INFORMATION: 3' Spacer C3 blocker
<220> FEATURE:
<221> NAME/KEY: misc_feature
<222> LOCATION: (12)..(13)
<223> OTHER INFORMATION: BHQ-2 Quencher

<400> SEQUENCE: 16
ttccatgcta tctctgggac caatggtact aagagg 36

<210> SEQ ID NO 17
<211> LENGTH: 29
<212> TYPE: DNA
<213> ORGANISM: Artificial Sequence
<220> FEATURE:
<223> OTHER INFORMATION: Probe D69-70-2_PRB_SHT
<220> FEATURE:
<221> NAME/KEY: misc_feature
<223> OTHER INFORMATION: 5' JA270
<220> FEATURE:
<221> NAME/KEY: misc_feature
<223> OTHER INFORMATION: 3' Spacer C3 blocker
<220> FEATURE:
<221> NAME/KEY: misc_feature
<222> LOCATION: (12)..(13)
<223> OTHER INFORMATION: BHQ-2 Quencher

<400> SEQUENCE: 17
ttccatgcta tctctgggac caatggtac 29

<210> SEQ ID NO 18
<211> LENGTH: 47
<212> TYPE: DNA
<213> ORGANISM: Artificial Sequence
<220> FEATURE:
<223> OTHER INFORMATION: Probe E484K_ML_PRB1
<220> FEATURE:
<221> NAME/KEY: misc_feature
<223> OTHER INFORMATION: 5' Coumarin
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (4)..(6)
<223> OTHER INFORMATION: D-Locked Nucleic Acid
<220> FEATURE:
<221> NAME/KEY: misc_feature
<222> LOCATION: (8)..(9)
<223> OTHER INFORMATION: BHQ-2 Quencher

<400> SEQUENCE: 18
tgttaaaggt tttaattgtt actttccttt acaatcatat ggtttcc 47

<210> SEQ ID NO 19
<211> LENGTH: 30
<212> TYPE: DNA
<213> ORGANISM: Artificial Sequence
<220> FEATURE:
<223> OTHER INFORMATION: Probe N501Y_HEX_PRB1
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (4)..(6)
<223> OTHER INFORMATION: D-Locked Nucleic Acid
<220> FEATURE:
<221> NAME/KEY: misc_feature
<222> LOCATION: (7)..(8)
<223> OTHER INFORMATION: BHQ-2 Quencher

<400> SEQUENCE: 19
cacttatggt gttggttacc aaccatacag 30

<210> SEQ ID NO 20
<211> LENGTH: 47
<212> TYPE: DNA
<213> ORGANISM: Artificial Sequence
<220> FEATURE:
<223> OTHER INFORMATION: Probe E484K_ML_FAM1
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (4)..(6)
<223> OTHER INFORMATION: D-Locked Nucleic Acid
<220> FEATURE:
<221> NAME/KEY: misc_feature
<222> LOCATION: (8)..(9)
<223> OTHER INFORMATION: BHQ-2 Quencher

<400> SEQUENCE: 20
tgttaaaggt tttaattgtt actttccttt acaatcatat ggtttcc 47

<210> SEQ ID NO 21
<211> LENGTH: 38
<212> TYPE: DNA
<213> ORGANISM: Artificial Sequence
<220> FEATURE:
<223> OTHER INFORMATION: Probe Y144_PRB
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (8)..(9)
<223> OTHER INFORMATION: BHQ-2 Quencher

<400> SEQUENCE: 21
tttgggtgtt taccacaaaa acaacaaaag ttggatgg 38

<210> SEQ ID NO 22
<211> LENGTH: 38
<212> TYPE: DNA
<213> ORGANISM: Artificial Sequence
<220> FEATURE:
<223> OTHER INFORMATION: Probe K417N4d
<220> FEATURE:
<221> NAME/KEY: misc_feature
<223> OTHER INFORMATION: 5' Coumarin
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (7)..(7)
<223> OTHER INFORMATION: D-Locked Nucleic Acid
<220> FEATURE:
<221> NAME/KEY: misc_feature
<222> LOCATION: (10)..(11)
<223> OTHER INFORMATION: BHQ-2 Quencher
<220> FEATURE:
<221> NAME/KEY: misc_feature
<222> LOCATION: (16)..(17)
<223> OTHER INFORMATION: D-Locked Nucleic Acid
<220> FEATURE:
<221> NAME/KEY: misc_feature
<222> LOCATION: (22)..(23)
<223> OTHER INFORMATION: D-Locked Nucleic Acid
<220> FEATURE:
<221> NAME/KEY: misc_feature
<222> LOCATION: (29)..(30)

<223> OTHER INFORMATION: D-Locked Nucleic Acid

<400> SEQUENCE: 22
tggaaatatt gctgattata attataaatt accagatg 38

<210> SEQ ID NO 23
<211> LENGTH: 37
<212> TYPE: DNA
<213> ORGANISM: Artificial Sequence
<220> FEATURE:
<223> OTHER INFORMATION: Probe L452R2-zx1
<220> FEATURE:
<221> NAME/KEY: misc_feature
<223> OTHER INFORMATION: 5' Coumarin
<220> FEATURE:
<221> NAME/KEY: misc_feature
<223> OTHER INFORMATION: 3' Spacer C3 Blockerr
<220> FEATURE:
<221> NAME/KEY: misc_feature
<222> LOCATION: (5)..(6)
<223> OTHER INFORMATION: BHQ-2 Quencher
<220> FEATURE:
<221> NAME/KEY: misc_feature
<222> LOCATION: (13)..(15)
<223> OTHER INFORMATION: D-Locked Nucleic Acid

<400> SEQUENCE: 23
taccggtata gattgtttag gaagtctaat ctcaaac 37

<210> SEQ ID NO 24
<211> LENGTH: 40
<212> TYPE: DNA
<213> ORGANISM: Artificial Sequence
<220> FEATURE:
<223> OTHER INFORMATION: Probe K417N4cs_J270
<220> FEATURE:
<221> NAME/KEY: misc_feature
<223> OTHER INFORMATION: 5' JA270
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (9)..(9)
<223> OTHER INFORMATION: D-Locked Nucleic Acid
<220> FEATURE:
<221> NAME/KEY: misc_feature
<222> LOCATION: (12)..(13)
<223> OTHER INFORMATION: BHQ-2 Quencher
<220> FEATURE:
<221> NAME/KEY: misc_feature
<222> LOCATION: (18)..(19)
<223> OTHER INFORMATION: D-Locked Nucleic Acid
<220> FEATURE:
<221> NAME/KEY: misc_feature
<222> LOCATION: (24)..(25)
<223> OTHER INFORMATION: D-Locked Nucleic Acid
<220> FEATURE:
<221> NAME/KEY: misc_feature
<222> LOCATION: (31)..(32)
<223> OTHER INFORMATION: D-Locked Nucleic Acid

<400> SEQUENCE: 24
actggaaata ttgctgatta taattataaa ttaccagatg 40

<210> SEQ ID NO 25
<211> LENGTH: 35
<212> TYPE: DNA
<213> ORGANISM: Artificial Sequence
<220> FEATURE:
<223> OTHER INFORMATION: Probe N439K_e3mC
<220> FEATURE:
<221> NAME/KEY: misc_feature
<223> OTHER INFORMATION: 5' HEX
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (4)..(7)
<223> OTHER INFORMATION: D-Locked Nucleic Acid
<220> FEATURE:
<221> NAME/KEY: misc_feature
<222> LOCATION: (9)..(10)
<223> OTHER INFORMATION: BHQ-2 Quencher
<220> FEATURE:
<221> NAME/KEY: misc_feature
<222> LOCATION: (12)..(12)
<223> OTHER INFORMATION: D-Locked Nucleic Acid
<220> FEATURE:
<221> NAME/KEY: misc_feature
<222> LOCATION: (16)..(16)
<223> OTHER INFORMATION: 2'-OMethyl
<220> FEATURE:
<221> NAME/KEY: misc_feature
<222> LOCATION: (16)..(16)
<223> OTHER INFORMATION: D-Locked Nucleic Acid
<220> FEATURE:
<221> NAME/KEY: misc_feature
<222> LOCATION: (20)..(20)
<223> OTHER INFORMATION: D-Locked Nucleic Acid

<400> SEQUENCE: 25
ctaaaaatct tgattctaag gttggtggta attat 35

<210> SEQ ID NO 26
<211> LENGTH: 38
<212> TYPE: DNA
<213> ORGANISM: Artificial Sequence
<220> FEATURE:
<223> OTHER INFORMATION: Probe D69-70_WT1_PRB
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (7)..(8)
<223> OTHER INFORMATION: BHQ-2 Quencher

<400> SEQUENCE: 26
tccatgctat acatgtctct gggaccaatg gtactaag 38

<210> SEQ ID NO 27
<211> LENGTH: 42
<212> TYPE: DNA
<213> ORGANISM: Artificial Sequence
<220> FEATURE:
<223> OTHER INFORMATION: Probe E484K_WT2L_PRB2
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (4)..(6)
<223> OTHER INFORMATION: D-Locked Nucleic Acid
<220> FEATURE:
<221> NAME/KEY: misc_feature
<222> LOCATION: (8)..(9)
<223> OTHER INFORMATION: BHQ-2 Quencher

<400> SEQUENCE: 27
tgttgaaggt tttaattgtt actttccttt acaatcatat gg 42

<210> SEQ ID NO 28
<211> LENGTH: 30
<212> TYPE: DNA
<213> ORGANISM: Artificial Sequence
<220> FEATURE:
<223> OTHER INFORMATION: Probe N501Y-WT_PRB
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (4)..(6)
<223> OTHER INFORMATION: D-Locked Nucleic Acid
<220> FEATURE:
<221> NAME/KEY: misc_feature
<222> LOCATION: (7)..(8)
<223> OTHER INFORMATION: BHQ-2 Quencher

<400> SEQUENCE: 28
cactaatggt gttggttacc aaccatacag 30

<210> SEQ ID NO 29
<211> LENGTH: 42
<212> TYPE: DNA
<213> ORGANISM: Artificial Sequence
<220> FEATURE:
<223> OTHER INFORMATION: Probe E484K_WT2L_COU1
<220> FEATURE:
<221> NAME/KEY: misc_feature
<223> OTHER INFORMATION: 5' Coumarin
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (4)..(6)
<223> OTHER INFORMATION: D-Locked Nucleic Acid
<220> FEATURE:
<221> NAME/KEY: misc_feature
<222> LOCATION: (8)..(9)
<223> OTHER INFORMATION: BHQ-2 Quencher

<400> SEQUENCE: 29
tgttgaaggt tttaattgtt actttccttt acaatcatat gg 42

<210> SEQ ID NO 30
<211> LENGTH: 42
<212> TYPE: DNA
<213> ORGANISM: Artificial Sequence
<220> FEATURE:
<223> OTHER INFORMATION: Probe N501Y-WT_COU1
<220> FEATURE:
<221> NAME/KEY: misc_feature
<223> OTHER INFORMATION: 5' Coumarin
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (4)..(6)
<223> OTHER INFORMATION: D-Locked Nucleic Acid
<220> FEATURE:
<221> NAME/KEY: misc_feature
<222> LOCATION: (8)..(9)
<223> OTHER INFORMATION: BHQ-2 Quencher

<400> SEQUENCE: 30
tgttgaaggt tttaattgtt actttccttt acaatcatat gg 42

<210> SEQ ID NO 31
<211> LENGTH: 38
<212> TYPE: DNA
<213> ORGANISM: Artificial Sequence
<220> FEATURE:
<223> OTHER INFORMATION: Probe K417N_wt8c
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (10)..(11)
<223> OTHER INFORMATION: BHQ-2 Quencher
<220> FEATURE:
<221> NAME/KEY: misc_feature
<222> LOCATION: (16)..(17)
<223> OTHER INFORMATION: D-Locked Nucleic Acid
<220> FEATURE:
<221> NAME/KEY: misc_feature
<222> LOCATION: (22)..(23)
<223> OTHER INFORMATION: D-Locked Nucleic Acid
<220> FEATURE:
<221> NAME/KEY: misc_feature
<222> LOCATION: (29)..(30)
<223> OTHER INFORMATION: D-Locked Nucleic Acid

<400> SEQUENCE: 31
tggaaagatt gctgattata attataaatt accagatg 38

<210> SEQ ID NO 32
<211> LENGTH: 38
<212> TYPE: DNA
<213> ORGANISM: Artificial Sequence
<220> FEATURE:
<223> OTHER INFORMATION: Probe K417N_wt8a1
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (6)..(8)
<223> OTHER INFORMATION: D-Locked Nucleic Acid
<220> FEATURE:
<221> NAME/KEY: misc_feature
<222> LOCATION: (10)..(11)
<223> OTHER INFORMATION: BHQ-2 Quencher
<220> FEATURE:
<221> NAME/KEY: misc_feature
<222> LOCATION: (16)..(17)
<223> OTHER INFORMATION: D-Locked Nucleic Acid

<400> SEQUENCE: 32
tggaaagatt gctgattata attataaatt accagatg 38

<210> SEQ ID NO 33
<211> LENGTH: 37
<212> TYPE: DNA
<213> ORGANISM: Artificial Sequence
<220> FEATURE:
<223> OTHER INFORMATION: Probe L452R_wt1-zx1
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' Spacer C3 Blocker
<220> FEATURE:

```
<221> NAME/KEY: misc_feature
<222> LOCATION: (5)..(5)
<223> OTHER INFORMATION: D-Locked Nucleic Acid
<220> FEATURE:
<221> NAME/KEY: misc_feature
<222> LOCATION: (6)..(7)
<223> OTHER INFORMATION: BHQ-2 Quencher
<220> FEATURE:
<221> NAME/KEY: misc_feature
<222> LOCATION: (16)..(17)
<223> OTHER INFORMATION: D-Locked Nucleic Acid

<400> SEQUENCE: 33

tacctgtata gattgtttag gaagtctaat ctcaaac                              37


<210> SEQ ID NO 34
<211> LENGTH: 40
<212> TYPE: DNA
<213> ORGANISM: Artificial Sequence
<220> FEATURE:
<223> OTHER INFORMATION: Probe K417N_wt8cs_J270
<220> FEATURE:
<221> NAME/KEY: misc_feature
<223> OTHER INFORMATION: 5' JA270
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (12)..(13)
<223> OTHER INFORMATION: BHQ-2 Quencher
<220> FEATURE:
<221> NAME/KEY: misc_feature
<222> LOCATION: (18)..(19)
<223> OTHER INFORMATION: D-Locked Nucleic Acid
<220> FEATURE:
<221> NAME/KEY: misc_feature
<222> LOCATION: (24)..(25)
<223> OTHER INFORMATION: D-Locked Nucleic Acid
<220> FEATURE:
<221> NAME/KEY: misc_feature
<222> LOCATION: (31)..(32)
<223> OTHER INFORMATION: D-Locked Nucleic Acid

<400> SEQUENCE: 34

actggaaaga ttgctgatta taattataaa ttaccagatg                           40


<210> SEQ ID NO 35
<211> LENGTH: 32
<212> TYPE: DNA
<213> ORGANISM: Artificial Sequence
<220> FEATURE:
<223> OTHER INFORMATION: Probe N439K_wte2
<220> FEATURE:
<221> NAME/KEY: misc_feature
<223> OTHER INFORMATION: 5' FAM
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (4)..(6)
<223> OTHER INFORMATION: D-Locked Nucleic Acid
<220> FEATURE:
<221> NAME/KEY: misc_feature
<222> LOCATION: (5)..(5)
<223> OTHER INFORMATION: 2' OMethyl
<220> FEATURE:
<221> NAME/KEY: misc_feature
<222> LOCATION: (9)..(10)
<223> OTHER INFORMATION: BHQ-2 Quencher
<220> FEATURE:
<221> NAME/KEY: misc_feature
<222> LOCATION: (16)..(16)
<223> OTHER INFORMATION: D-Locked Nucleic Acid
```

<220> FEATURE:
<221> NAME/KEY: misc_feature
<222> LOCATION: (16)..(16)
<223> OTHER INFORMATION: 2' OMethyl

<400> SEQUENCE: 35
ctaacaatct tgattctaag gttggtggta at 32

<210> SEQ ID NO 36
<211> LENGTH: 36
<212> TYPE: DNA
<213> ORGANISM: Artificial Sequenced
<220> FEATURE:
<223> OTHER INFORMATION: Probe WUHAN-4P_COU6QC3
<220> FEATURE:
<221> NAME/KEY: misc_feature
<223> OTHER INFORMATION: 5' Coumarin
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (6)..(7)
<223> OTHER INFORMATION: BHQ-2 Quencher

<400> SEQUENCE: 36
tcatcgtcaa caacctagac aaatcagctg gttttc 36

<210> SEQ ID NO 37
<211> LENGTH: 42
<212> TYPE: DNA
<213> ORGANISM: Artificial Sequence
<220> FEATURE:
<223> OTHER INFORMATION: Blocking Probe E484K_WT2L_NO_DYE
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (4)..(6)
<223> OTHER INFORMATION: D-Locked Nucleic Acid

<400> SEQUENCE: 37
tgttgaaggt tttaattgtt actttccttt acaatcatat gg 42

<210> SEQ ID NO 38
<211> LENGTH: 30
<212> TYPE: DNA
<213> ORGANISM: Artificial Sequence
<220> FEATURE:
<223> OTHER INFORMATION: Blocking Probe N501Y-WT_NO_DYE
<220> FEATURE:
<221> NAME/KEY: misc_feature
<223> OTHER INFORMATION: 3' Spacer C3 Blocker
<220> FEATURE:
<221> NAME/KEY: misc_feature
<222> LOCATION: (4)..(6)
<223> OTHER INFORMATION: D-Locked Nucleic Acid

<400> SEQUENCE: 38
cactaatggt gttggttacc aaccatacag 30

-continued

```
<210> SEQ ID NO 39
<211> LENGTH: 38
<212> TYPE: DNA
<213> ORGANISM: Artificial Sequence
<220> FEATURE:
<223> OTHER INFORMATION: Blocking Probe LNAD69-70_WT1_NO_DYE
<220> FEATURE:
<221> NAME/KEY: misc_feature
<223> OTHER INFORMATION: 3' Spacer C3 Blocker

<400> SEQUENCE: 39

tccatgctat acatgtctct gggaccaatg gtactaag                          38
```